US006423827B1

(12) United States Patent
Levitt et al.

(10) Patent No.: US 6,423,827 B1
(45) Date of Patent: Jul. 23, 2002

(54) LIMBIC SYSTEM-ASSOCIATED MEMBRANE PROTEIN

(75) Inventors: Pat Ressler Levitt, Wyncote, PA (US); Aurea Pimenta, Princeton, NJ (US); Itzhak Fischer, Blue Bell; Victoria Zhukareva, Philadelphia, both of PA (US)

(73) Assignee: University of Medicine and Dentistry of New Jersey, University Heights, NJ (US)

( * ) Notice: Subject to any disclaimer, the term of this patent is extended or adjusted under 35 U.S.C. 154(b) by 0 days.

(21) Appl. No.: 09/135,080

(22) Filed: Aug. 17, 1998

Related U.S. Application Data

(62) Division of application No. 08/414,657, filed on May 15, 1995, now Pat. No. 5,861,283.

(51) Int. Cl.⁷ ..................... C07K 14/435; C07K 14/705

(52) U.S. Cl. .......................................... 530/350; 930/10

(58) Field of Search ................................ 530/350, 300; 930/10

(56) References Cited

PUBLICATIONS

Zacco et al. J. Neurosci. 10: 73–90, 1990.*
Rudinger, In "Peptide Hormones" (J.A. Parsons) University Park Press, Baltimore, pp. 1–7, 1976.*
Pimenta, et al., The partial nucleotide sequence of a cDNA encoding the limbic system–associated membrane protein (LAMP), Molecular Biology of the Cell, vol. 3, No. Suppl., 1992, p. 323A, Thirty–second Annual Meeting of the American Society for Cell Biology, Denver, CO, Nov. 15–19, (Abstract), 1992.
Pimenta, et al., "The limbic system–associated membrane protein is an lg superfamily member that mediates selective neuronal growth and axon targeting", Neuron, vol. 15, Aug. 1995, pp. 287–297.
Pimenta, et al., "cDNA cloning and structural analysis of the human limbic–system–associated membrane protein (LAMP)", Gene, NL, Elsevier Biomedical Press, vol. 170, No. 2, May 8, 1996. pp. 189–195.
Friedman, GENE THERAPY FOR NEUROLOGICAL DISORDERS, Elsevier Science Ltd., (TIG) vol. 10, No. 6, pp. 210–214 (1994).
David C. Litzinger et al., Biochimica et Biophysica Acta, 1113:201–227 (1992).
Philip L. Feigner, Advanced Drug Delivery Reviews, 5:163–187 (1990).
Cary Lai et al., Proc. Natl. Sci. USA, 84:4337–4341 (1987).
C. Helene, Anti–Cancer Drug Design, 6:569–584 (1991).
Levitt, Science 223:299–301, 1984.
Keller et al., Neuron 3:551–556, 1989.
Pennypacker et al., ABSTRACT to the 1989 Annual Meeting of the Socieity for Neuroscience.
Zukhareva and Levitt, Molec. Biol. of the Cell 3:197A (ABSTRACT), 1992.
Zukhareva and Levitt, Soc. for Neuroscience Abstracts 19:1291 (ABSTRACT to the 1993 Annual Meeting of the Society for Neuroscience), 1993.
Pimenta et al., Soc. for Neuroscience Abstracts 19:689 (ABSTRACT), 1993.
Pimenta et al., Molec. Biol. of the Cell 5:232a (ABSTRACT), 1994.
Zhukhareva et al., Molec. Biol. of the Cell 5:436a (ABSTRACT), 1994.
Levitt et al., Molec. Biol. of the Cell 5:232a (ABSTRACT), 1994.
Zacco et al., J. Neuroscience 10:73–90, 1990.
Chesselet et al., Neurosci. 40:725–733, 1991.
Ferri and Levitt, Cerebral Cortex 3:187–198, 1993.
Keller and Levitt, Neuroscience 28:455–474, 1989.
Zhukareva and Levitt, Development, vol. 121, 1995 (pre–print).
Pearson and Lipman, Proc. Natl. Acad. Sci. USA 85:2444–2448, 1988.
Schofield et al., EMBO J. 8:489–495, 1989.
Lippman et al., Gene 117:249–254, 1992.
Struyk, et al., J. Neurosci., 15:2141–2156, 1995.
Seeger et al., Cell 55:589–600, 1988.
Arquint et al., Proc. Natl. Acad. Sci. U.S.A. 84:600–604, 1987.
Salzer et al., J. Cell Biol 104:957–965, 1987.
Karlstron et al., Development 118:509–522, 1993.
Cunningham et al., Science 236:799–806, 1987.
Dulac et al., Neuron 8:323–334, 1992.
Furley et al., Cell 61:157–170, 1990.
Grenningloh et al., Cell 67:45–57, 1991.
Moos et al., Nature 334:701–703, 1988.
Burgoon et al., J. Cell Biol. 112:1017–1029, 1991.
Heijne, Nucleic Acids Res. 14:4683–4690, 1986.
Cross, Ann. Rev. Cell Biol. 6:1–39, 1990.
Ferguson and Williams, Ann. Rev. Biochem. 57:285–320, 1988.
Gerber et al., J. Biol. Chem. 267:18168–12173, 1992.
Kreuter, Infection 19, Supp. 4:S224–S228, 1991.

(List continued on next page.)

Primary Examiner—Gary L. Kunz
Assistant Examiner—Robert C. Hayes
(74) Attorney, Agent, or Firm—Dechert

(57) ABSTRACT

The present invention is directed to nucleic acid sequences encoding a limbic-system associated membrane protein ("LAMP") and to purified proteins with LAMP activity. LAMP is a self-binding, antibody-like cell surface adhesion protein, the presence of which on one neuron of the limbic system stimulates the formation of connections with adjacent neurons. The invention provides a nucleic acid sequence encoding a polypeptide with at least about 90% homology to a LAMP self-binding domain, and corresponding proteins. The invention also provides nucleic acids that hybridize to LAMP encoding nucleic acids.

18 Claims, 15 Drawing Sheets

OTHER PUBLICATIONS

Goedel et al., *Proc. Natl. Acad. Sci. USA* 76:106–110, 1979.
Chou and Fasman, *Adv. Enzymol*, 47:45–149, 1978.
Eisenberg et al., *Proc. Natl. Acad. Sci. USA* 81: 140–144, 1984.
Engleman et al., *Ann. Rev. Biophys. Chem.* 15:321–353, 1986.
McLachlin, et al., *Progr. Nucl. Acids Res. Mol. Biol.* 38:91–135 (1990).
Karlsson, *Blood* 78:2481–2492 (1991).
Einerhand and Valerio, *Curr. Top. Microbiol. Immunol.* 177:217–235 (1992).
Morsy et al., *J.A.M.A.* 270:2338–2345 (1993).
Dorudi et al., *British J. Surgery* 80:566–572 (1993).
Matsudaira, *J. Biol. Chem.* 262:10035–10038, 1987.
Henzel et al., *J. Chromatogr.* 404:41–52, 1987.
Sweadner, *J. Neurosci.* 3:2504–2517, 1983.
Haug, *Adv. Anat. Embryol. Cell Biol.* 47:1–71, 1973.
H. J. Lee et al., *Dev. Brain Res.* 52:219–228, 1990.
Schulz et al. *Principles of Protein Structure*, Springer–Verlag, pp. 14–16 & 108–130, 1978.
Kyte and Doolittle, *J. Mol. Biol.* 157:105–132, 1982.
Chou and Fasman, *Biochemistry* 13:211–222, 1974.
Needleman and Wunsch, *J. Mol. Biol.* 48:443–453, 1970.
Smith and Waterman, *Adv. Appl. Math.* 2:482–489, 1981.
Crooke, *Anti–Cancer Drug Design* 6:609–646, 1991.
Boutorin et al., *FEBS Lett.* 254:129–132, 1989.
Shea et al, *Nucleic Acids Res.* 18:3777–3783, 1990.
Agris et al., *Biochemistry* 25:6268–6275, 1986.
Cazenave and Helene in *Antisense Nucleic Acids and Proteins:Fundamentals and Applications*, Mol and Van der Krol, eds., pp. 47–93, Marcel Dekker, New York, 1991.
Milligan et al. in *Gene Therapy For Neoplastic Diseases*, Huber and Laso, eds., pp. 228–241, New York Academy of Sciences, New York, 1994.
Farhood et al., *Ann. N.Y. Acad. Sci.* 716:23–35, 1994.
Boris–Lawrie and Temin,*Ann. N.Y. Acad. Sci.*, 716:59–71 (1994).
Wu and Wu, *Biochemistry*, 27:887–892, 1988.
Behr et al., *Proc. Natl. Acad Sci U.S.A.* 86:6982–6986, 1989.
Graham and Van der Eb, *Virology* 52:456–457, 1973.
Sompayrac and Danna, *Proc. Natl. Acad. Sci.* 12:7575–7578, 1981.
Potter et al., *Proc. Natl. Acad. Sci.* 81:7161–7165, 1984.
Gitman et al., *Proc. Natl. Acad. Sci. U.S.A.* 82:7309–7313, 1985.
Wang and Huang, *Proc. Natl. Acad. Sci.* 84:7851–7855, 1987.
Akli, *Nature Genetics* 31:224–228, 1993.
Baldino et al., *Methods in Enzymology* 168:761–777, 1989.
Emson et al., *Methods in Enzymology* 168:753–761, 1989.
Harper et al., *Methods in Enzymology* 151:539–551, 1987.
Angerer et al., *Methods in Enzymology* 152:649–661, 1987.
Wilcox et al., *Methods in Enzymology* 124:510–533, 1986.
Sanger et al., *Proc. Natl. Acad. Sci. USA* 74:5463–5467, 1977.

* cited by examiner

```
Rat-nt  gtggccagcagcgcgcacacgcgcgagtccaccgctgaccaactcgccgaggccaccatggtc    61
Rat-AA                                                           M  V     2
Mo-AA                                                            -  -

Rat-nt  gggagagttcaacctgatcggaaacagttgccactgtcctgtctgcctt              121
Rat-AA   G  R  V  Q  P  D  R  K  Q  L  P  L  V  L  L  R  L  L  C  L    22
Hu-nt   ------------------g----------------------------------t----
Hu-AA    -  -  -  -  -  -  -  -  -  -  -  -  -  -  -  -  -  S  H  -
Mo-AA    -  -  -  -  -  -  -  -  -  -  -  -  -  -  -  -  -  -  -  -

Rat-nt  cttcccacaggactgcccgttcgcagcgtggattttaaccgaggcacgacaacatcacc     181
Rat-AA   L  P  T  G  L  P  V  R  S  V  D  F  N  R  G  T  D  N  I  T    42
Hu-nt   ----------------------t-----------------------------------
Hu-AA    -  -  -  -  -  -  -  -  -  -  -  -  -  -  -  -  -  -  -  -
Mo-AA    -  -  -  -  -  -  -  -  -  -  -  -  -  -  -  -  -  -  -  -

Rat-nt  gtgaggcaggggggacacggccatcctcaggtgtgtggtagaagacaagaactcgaaagtg    241
Rat-AA   V  R  Q  G  D  T  A  I  L  R  C  V  V  E  D  K  N  S  K  V    62
Hu-nt   ------------------a------------------tc----------a--g-----
Hu-AA    -  -  -  -  -  -  -  -  -  -  -  -  -  L  -  -  -  -  -  -
Mo-AA Rat-nt  gcctggttgaaccgctctggcatcatcttcgctggacacgacaagtggtctctgaccct     301
Rat-AA   A  W  L  N  R  S  G  I  I  F  A  G  H  D  K  W  S  L  D  P    82
Hu-nt   ------------t-------t-----------t---------------------------a
Hu-AA    -  -  -  -  -  -  -  -  -  -  -  -  -  -  -  -  -  -  -  -
```

FIG. 3A
PART 1 OF 4

```
Rat-nt  cgggttgagctggagaaacgccatgctctctggaatacagcctccgaatccagaaggtgat  361
Rat-AA   R  V  E  L  E  K  R  H  A  L  E  Y  S  L  R  I  Q  K  V  D   102
Hu-nt   ------------------------t---------s-------------------------
Hu-AA    -  -  -  -  -  -  -  -  -  -  -  -  -  -  -  -  -  -  -  -

Rat-nt  gtctatgatgaaggatccctacacatgtcagttcagacacagcatgagcccaagacctct  421
Rat-AA   V  Y  D  E  G  S  Y  T  C  S  V  Q  T  Q  H  E  P  K  T  S   122
Hu-nt   ---------g---t---------------------------------------------c
Hu-AA    -  -  -  -  -  -  -  -  -  -  -  -  -  -  -  -  -  -  -  -

Rat-nt  caagtttacttgattgtacaagttccaccaaagatctccaacatctcctcggatgtcact  481
Rat-AA   Q  V  Y  L  I  V  Q  V  P  P  K  I  S  N  I  S  S  D  V  T   142
Hu-nt   ----------------c----------------------t--------------------
Hu-AA    -  -  -  -  -  -  -  -  -  -  -  -  -  -  -  -  -  -  -  -

Rat-nt  gtgaatgagggcagcaatgtaaccctggtctgcatggccaatgggcgccctgaacctgtt  541
Rat-AA   V  N  E  G  S  N  V  T  L  V  C  M  A  N  G  R  P  E  P  V   162
Hu-nt   ----------------c---g--t---------------------c---t----------
Hu-AA    -  -  -  -  -  -  -  -  -  -  -  -  -  -  -  -  -  -  -  -

Rat-nt  atcacctggagacacctacaccactggaagagaatttgaaggagaagaatatctg  601
Rat-AA   I  T  W  R  H  L  T  P  L  G  R  E  F  E  G  E  E  E  Y  L   182
Hu-nt   ------------------ac------g-----------------------------
Hu-AA    -  -  -  -  -  -  T  -  -  -  -  -  -  -  -  -  -  -  -  -
```

FIG. 3B
PART 2 OF 4

```
Rat-nt  gagatcctaggcatcaccagggaacagtcaggcaaatatgagtgcaaggctgccaacgag  661
Rat-AA   E  I  L  G  I  T  R  E  Q  S  G  K  Y  E  C  K  A  A  N  E   202
Hu-nt   -----------t-----------g-------------------g---------------
Hu-AA    -  -  -  -  -  -  -  -  -  -  -  -  -  -  -  -  -  -  -  -

Rat-nt  gtctcctccgcggatgtcaaacaagtcaaggtcactgtgaactatccaccaccatcaca  721
Rat-AA   V  S  S  A  D  V  K  Q  V  K  V  T  V  N  Y  P  P  T  I  T   222
Hu-nt   ----------g--------------------------------------t---------
Hu-AA    -  -  -  -  -  -  -  -  -  -  -  -  -  -  -  -  -  -  -  -

Rat-nt  gagtctaagagcaatgaagccaccacaggacgacaagcttccctcaaatgtgaagcctca  781
Rat-AA   E  S  K  S  N  E  A  T  T  G  R  Q  A  S  L  K  C  E  A  S   242
Hu-nt   ---a---c-----------------------------------a-------g--------g
Hu-AA    -  -  -  -  -  -  -  -  -  -  -  -  -  -  -  -  -  -  -  -

Rat-nt  gcggtgcctgcacctgactttgagtggtaccgggatgacaccaggataaacagtgcaaac  841
Rat-AA   A  V  P  A  P  D  F  E  W  Y  R  D  D  T  R  I  N  S  A  N   262
Hu-nt   --a--------------------------------------------t-----c-----t
Hu-AA    -  -  -  -  -  -  -  -  -  -  -  -  -  -  -  -  -  -  -  -

Rat-nt  ggccttgagattaagagcactgagggccagtccctgacggtgaccaacgtcactgag  901
Rat-AA   G  L  E  I  K  S  T  E  G  Q  S  S  L  T  V  T  N  V  T  E   282
Hu-nt   -----------------------g-----------------------------------
Hu-AA    -  -  -  -  -  -  -  -  -  -  -  -  -  -  -  -  -  -  -  -
```

FIG. 3C
PART 3 OF 4

```
Rat-nt  gaacactacggcaactatacctgtgtggctgccaacaagctcggcgtcaccaatgccagc  961
Rat-AA   E  H  Y  G  N  Y  T  C  V  A  A  N  K  L  G  V  T  N  A  S   302
Hu-nt   ---g-------------c-------------------------g----------------
Hu-AA Rat-nt  ctagtcctttcAgacccgggtcggtgagaggaatcaacggatccatcagtctggccgta 1021
Rat-AA   L  V  L  F  R  P  G  S  V  R  G  I  N  G  S  I  S  L  A  V   322
Hu-nt   ---------------t----------------------a--t------------------
Hu-AA Rat-nt  ccactgtggctgctgcagcgtccctgttctgcctttctcagcaaatgttaatagaataaa 1081
Rat-AA   P  L  W  L  L  Q  R  S  L  F  C  L  L  S  K  C  (SEQ ID      338
Hu-nt   -------------------------g---t----c---                NO: 4)
Hu-AA                  -              -  L           (SEQ ID NO:1)
                                                    (SEQ ID NO: 2)

Rat-nt  aatttaaaaataattacaaaacacacaaaaatgcgtcacacagatacacagagaaatac 1141
                                                       (SEQ ID NO:3)

Rat-nt  gagagagagaaagtacaagatgggggagactattgtttcacaagattgtgtgttat    1201

Rat-nt  aaatgaaggggggatatgaaaaaatgaagaaatac  (SEQ ID NO:3)          1238
```

FIG. 3D
PART 4 OF 4

```
CTGCAGTATG  CCTTCCTATC  CATGTGTATG  TAACTCCATT  TGTCAAGGTT   50
TGCATTTCTT  TCTTGCCATG  CCTTCCCTCT  CCTTTCCTGG  ACCCTTTCTC  100
CTGTCCTTTT  ACAGCTTAAG  TCCACCTCCC  CTTCCCTGTC  TTAACAGTAC  150
CTCTGAGCCC  CATCCCCTCT  TCTTAAGGAA  ATCAGCCAGG  CCTCAGATGG  200
AGCTGTTGTC  CTGACAACCC  AAAGGCGCAT  CAGGCTTTCA  TTGAGGCTGG  250
                                                           -400
CTGCTGGTGA  AGAGGGCAGT  TGTGCAAAGC  AAGGGGCCAC  GCTGAGGGGT  300
                                                           -350
GGGAGGAGGG  GATGACGTGG  TGGGGCTGTT  GAAAACCAGC  AGGGTAGGGG  350
            CREB consensus                                 -300
```

FIG. 5A
PART 1 OF 5

```
GGAGGTGCTG AGTAGAGAGA GAACAGGGAC TGGAGGGAGA AACAAGAAAG    400
           AP-1 consensus                         |
                                                 -250

AGGAGGGGGA GAGAGCTCCT GGGTTGCTGC CGCTACTGCT GCTGCTGCTG    450
                                                     |
                                                    -200

CAAGAGGCTG TTTCTTTACT CTCCCTGGCA GGCTCTCCCTG CTGCCTGGGA   500
                                                     |
                                                    -150

AAGTGGGTTA CAGAGGGAAG CAGCTCAGCC CAGACGCTGG CAGAGAAGCA    550
                     SP-1 consensus                  |
                                                    -100

GCCAGCTACA GAGAGTCTAA GGAAGCACCC CTGCCATTGA CAGTCGCCTC    600
                                                     |
                                                     -50
```

FIG. 5B

```
CTCATCATTA AAGCATTTTA TATTGCACT  CTTCCTTCGG AAAATTTGTT         650
           ────────── ─────────                    ↰
               TATA consensus

CCTCCACTTT CTCCCCGACT CCTGCTTGGA TTTGATGAGG GCTTTGTTAA         700

ATCCCAGAGG AAAAGAGACT AAGCGAGGGA AAGAGCAAGG CAAAGTGGAA         750

GGGAGTGCGC GCTGGACCCG CCCGAGCAGC CTTGGCAGTG GCTGCCAGCC         800

CCGGCGGCTA GAGCCCCTCT CCGTGTCCAG CAGGCGGCAC ACGCAGTCCA         850

CCGGCGGACCA ACTCGCCCGAG GCCACC ATG GTC GGG AGA GTT CAG        894
                              Met Val Gly Arg Val Gln
                               1               5

CCC GAT CGG AAA CAG TTG CCG CTG GTC CTA CTG AGA TCT TCC CAC   939
Pro Asp Arg Lys Gln Leu Pro Leu Val Leu Leu Arg Ser Ser His
            10                      15                  20
```

FIG. 5C
PART 3 OF 5

```
CTT CTT CCC ACA GGA CTG CCC GTT CGC AGC GTG GAT TTT AAC CGA   984
Leu Leu Pro Thr Gly Leu Pro Val Arg Ser Val Asp Phe Asn Arg
                 25                  30                  35

GGC ACG GAC AAC ATC ACC GTG AGA CAG GGG GAC ACG GCC ATC CTC  1029
Gly Thr Asp Asn Ile Thr Val Arg Gln Gly Asp Thr Ala Ile Leu
                 40                  45                  50

AGG TAGGGCTT GCGAGCAACT                                      1050
Arg

TTTCTGGTGT GTGTGTGTGT GTGTGTGTGT GTGTGTGTGT GTGTGTGTGT       1100

GTGTAATAGT GAACTCCAGC TGCCCTGGGT TAGTGGGCGT GTGTGTGTGT       1150

GTGTGTGTGT GTGTGTGTCC CTTACGTTAC TCGACTTGAA GATTAGCCA        1200

GGAACAAAAT TTAAGGCGAG TCTGGTCCCT GTCAAGAGCC AAGGGTGCTT       1250

TTGGAATGTT GTTCCGTTCT TTGAATGTTG TTTTCTCTAG TCAAGAAAGC       1300
                                            AP-1 consensus CGAACTTTAT CTATGGCATT AGTGGCATTG GGCTGTATCA TGCTGTGGTA       1350
           Hox 1.3 consensus

ATTGCTCACG CTTGGCACTT AGACTTTTGT TGAGATTCTT CTATTCAGAC       1400
```

FIG. 5D
PART 4 OF 5

```
ACAAGAGTTG TTGAGTTATG GCTTTCAAAA CGTGGTACGC AAGGCTGCAT        1450
TCTCTTGTTC GTGTGTGTGT GTGTGTGTGT GTGTGTGTGT GTGTGTGTGT        1500
GTGTTGCTCA GCAAGGCTCA GTCTGCCCTA GCAGTAGTTC CTGATAGAAG        1550
ACTTTCTGTA AAGATCTCTG AATTGACATC ATAGGCAATA AATCAATCTT        1600
ACAACTTTGG CATGATTACT GGGAATGTGG ACAGAAATCA                   1650
ACACGAGAAT GAGAGAACGG AAGGAAAAGGA CAGAGGAGGA TCCAGCCTAA TGGCAGGCCG  1700
TTAAGAATAG AAAACTTAAA CAGAGGAGGA GAAGGCATTA ACCTGATATT        1750
ACATTAGATA CTACAAATTG ATCATTGAGT TCAAAGTCTT ATGCTTATGC        1800
AGCTCTGCCA ACGTCCGCAA TATAATTTGG GATGGAAATT TGGAAAAGCT T      1851
(SEQ ID NO:5)
```

FIG. 5E
PART 5 OF 5

FIG. 6A

```
Rat    aggcaaatatgagtgcaaggctgccaacgaggtctcctccgcgatgtcaacaagtcaagtcactgtgaactattcaccaccatcac    665
Human  ------------------------a----------------g--------------------------------------t----
Human   G  K  Y  E  Ⓒ K  A  A  N  E  V  S  S  A  D  V  K  Q  V  K  V  T  V  N  Y  P  P  T  I  T    222

Rat    agagtctaagaggagcaatgaagccaccacaggacgacacaagcttccctcaaatgtgaagcctgcctgcctgcacctgactttgagtggta    755
Human  ----a--c----------------------------------------------g---a----------g-a--------------
Human   E  S  K  S  N  E  A  T  T  G  R  Q  A  S  L  K  Ⓒ E  A  S  A  V  P  A  P  D  F  E  W  Y    252

Rat    ccgggatgacaccaggataaacagtgcaaacggccttgagattaagagcactgagggccagtcctccctgacggtgaccaacgtcactga    845
Human  -------------------t----------------------c--t----------------------------------t-----
Human   R  D  D  T  R  I  N  S  A  N  G  L  E  I  K  S  T  E  G  Q  S  S  L  T  V  T  N  V  T  E    282

Rat    ggaacactacggcaactacctgtggctgccaacaagctcggctgccaccatgccagcctagtcctctttcagacccgggtcggtgag      935
Human  --g-----------c-------------------------------------g--g--------------t---------------
Human   E  H  Y  G  N  Y  T  Ⓒ V  A  A  N  K  L  G  V  T  N  A  S  L  V  L  F  R  P  G  S  V  R    312

Rat    aggaatcaacggatccatcagtctggccgtaccactgtggctgctgcagcgtccctgttctgccttcccaccaaatgttaatagaataa    1025
Human  ---------a--t--------------------------------------a--t--c---[////////////////////](SEQ ID NO: 1)
Human   G  I  N  G  S  I  S  L  A  V  P  L  W  L  L  A  A  S  L  L  [C  L  L  S  K  C  .] (SEQ ID NO: 2)  338

Rat    aaatttaaaaataattacaaaacacacaaaaatgctcacacagatacagagagagagagagaaagtacaagatgggggg    1115

Rat    agactattgtttcacaagattgtgtgtttataaatgaaggggggatatgaaaaaatgaagaaaatac (SEQ ID NO: 3)
```

FIG. 6B (CONTINUED)

LIMBIC SYSTEM-ASSOCIATED MEMBRANE PROTEIN

This application is a divisional of U.S. application Ser. No. 08/414,657, filed May 15, 1995, now U.S. Pat. No. 5,861,283.

Part of the work performed during the development of this invention utilized United States Government Funds under National Institutes of Health Grant 5 R37 MH45507. The government has certain rights in the invention.

The present invention is directed to nucleic acid sequences encoding a limbic-system associated membrane protein ("LAMP") and to purified proteins with LAMP activity. LAMP is a self-binding, antibody-like cell surface adhesion protein, the presence of which on one neuron of the limbic system stimulates the formation of connections with adjacent neurons.

A monoclonal antibody, 2G9, that bound to the cell surface of certain neurons, mostly limbic system or limbic system-connected neurons had been identified. Levitt, Science 223:299–301, 1984. This antibody has been confirmed to be specific for LAMP. Explanted neurons of the septum express the 2G9 antigen and, in culture, normally will invade explanted tissue from the hippocampus. In 1989, it was reported that 2G9 blocked that invasive process. Keller et al., Neuron 3:551–561, 1989. Efforts were made to clone the antigen using 2G9. In 1989, these efforts lead to the submission to the Society of Neuroscience of an erroneous abstract reporting that the antigen had been cloned. Efforts to clone the antigen using the antibody have proved unsuccessful.

Immunochemical studies indicate that the antigen is a 64–68 kDa glycoprotein that is expressed by cortical and subcortical neurons of the limbic system. These brain areas form functional circuits involved in memory, learning, mood, affect, cognitive behavior and central autonomic regulation. The antigen is also expressed by neurons having interconnections with limbic brain areas. Early in development, the antigen is expressed on limbic-related neurons. During pathway formation and differentiation, the antigen is expressed transiently on neural growth cones and axons.

The immunochemistry data indicate that the antigen, now designated LAMP, is a cell-surface adhesion molecule involved in directing the growth and differentiation of certain neurons. LAMP, when purified using the monoclonal antibody and coated onto tissue culture plates, induces adhesion and the growth of neuritic processes of certain limbic neurons, but generally not of non-limbic neurons.

SUMMARY OF THE INVENTION

Despite sustained efforts to isolate the gene for the 2G9 antigen, it is only now that the nucleic acid encoding LAMP has been identified. It is herein designated SEQ ID NO: 1 for the human LAMP (SEQ ID NO:2) and SEQ ID NO: 3 for the entire protein-encoding rat sequence (SEQ ID NO:41). The portions of SEQ ID NO: 3 encompassing only the open reading frame are designated SEQ ID NO: 7. These sequences encode all or part of polypeptides of 338 amino acids and indicate that the protein is highly conserved, since the human and rat sequences differ in only four amino acid residues (approximately 99% homologous).

As indicated in FIG. 2, the sequence data indicate that LAMP has a three domain immunoglobin structure. Studies with phosphatidyl inositol ("PI") specific phospholipase C indicate that LAMP is bound to the cell membrane via a PI linkage. Thus, LAMP is much like other adhesion molecules of the immunoglobin superfamily that are attached to the cell surface by a PI linkage, such as TAG-1, Thy-1 and a form of NCAM. LAMP differs from these adhesion molecules in the specificity of its target tissues. The immunoglobulin domains of LAMP make up the binding or self-adhesion domain of LAMP.

In a first embodiment, the invention relates to a nucleic acid having a sequence encoding all of or a fragment of a LAMP effective to bind to a native LAMP at the cell surface of a neuron. In a further preferred embodiment, the nucleic acid encodes a water-soluble fragment of a LAMP. In still another preferred embodiment, the nucleic acid is a full-length-LAMP-encoding nucleic acid.

In yet another embodiment, the invention provides a nucleic acid encoding a mutant of the LAMP or fragment of the first embodiment.

In a further embodiment, the invention relates to a fragment of LAMP or a mutated LAMP fragment effective to bind to a native LAMP at the cell surface of a neuron to inhibit or stimulate the biological activity of the native LAMP.

In other embodiments, the invention relates to methods of treating disease, methods of diagnosing a developmental, psychotic or affective disorder, methods for detecting and measuring LAMP, nucleic acid polymerase chain reaction ("PCR") primers, tissues histochemically stained using the nucleic acids of the invention, cells transformed with the nucleic acids of the invention, vectors comprising the nucleic acids of the invention (in sense or antisense orientation), methods of transforming stem cells to promote differentiation to limbic system neurons or neurons forming connections to limbic system neurons, methods of using such transformed stem cells to treat a neurological disease, reagents for targeting a biological agent to the limbic system, nucleic acids for creating cell lines and transgenic animals for testing biological agents for their ability to interfere with the activity of LAMP, methods of targeting limbic cells for gene therapy by functionally attaching the gene sought to be expressed to a LAMP promoter (see SEQ ID NO: 5 and FIG. 5), and nucleic acids defining cell-type specific LAMP promoters.

Still another embodiment of the invention uses the nucleic acid of the invention, including the PCR primers, to probe for LAMP-gene polymorphisms associated with diseases that affect the limbic system. These diseases include, without limitation, schizophrenia, familial epilepsy, manic-depression, obsessive-compulsive disorder, mood disorders and other affective psychiatric disorders.

BRIEF DESCRIPTION OF THE DRAWINGS

FIGS. 3A–B shows the cDNA (SEQ ID NOs: 1 and 3, respectively) and protein sequence (SEQ ID NOs: 2 and 4, respectively) for human and rat LAMP, plus the protein sequence of a fragment of mouse LAMP (see, SEQ ID NOs:5 and 6)

FIGS. 5A–B displays a portion of the mouse genomic sequence for the LAMP gene, including 647 residues of the 5' untranscribed portion of the gene.

Figure 6A:
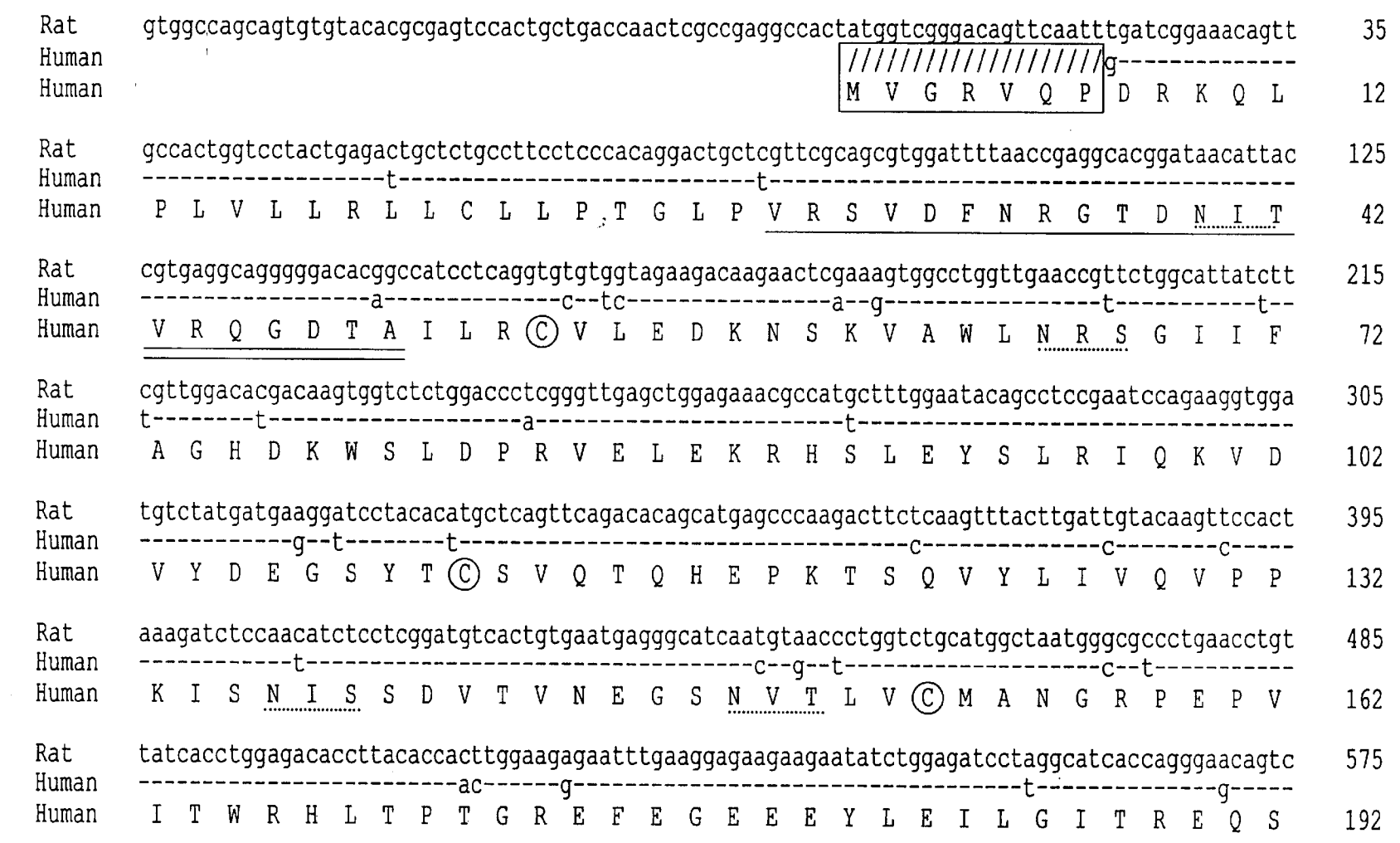

FIGS. 6A–B shows an alternate comparison of the rat and human LAMP sequences.

DETAILED DESCRIPTION OF THE INVENTION

Figure 1:
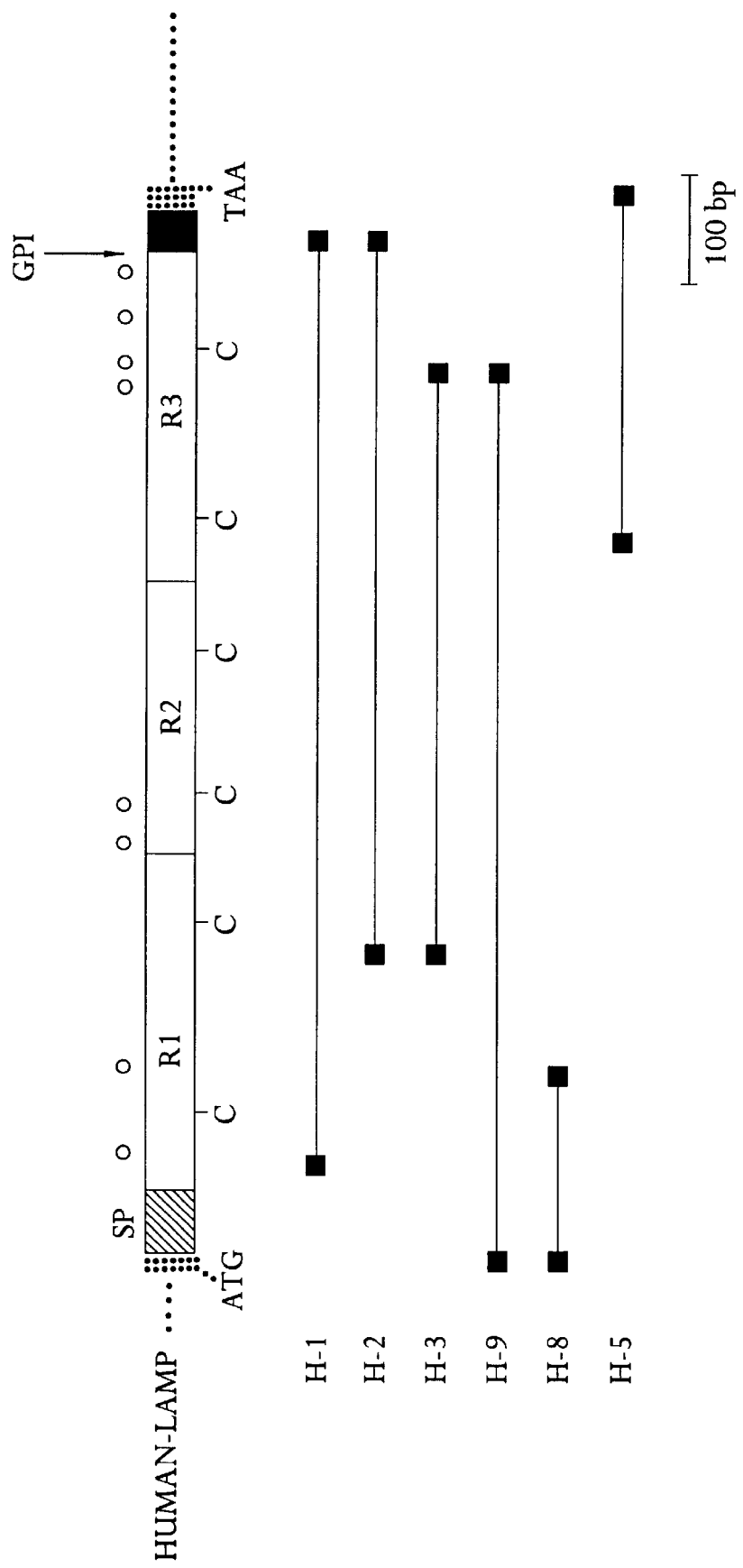
FIG. 1 shows a schematic representation of LAMP mRNA, including the open reading frame, its signal peptide, its hydrophobic C-terminus (required for processing of the PI anchor), and eight consensus glycosylation sites.
Figure 2:
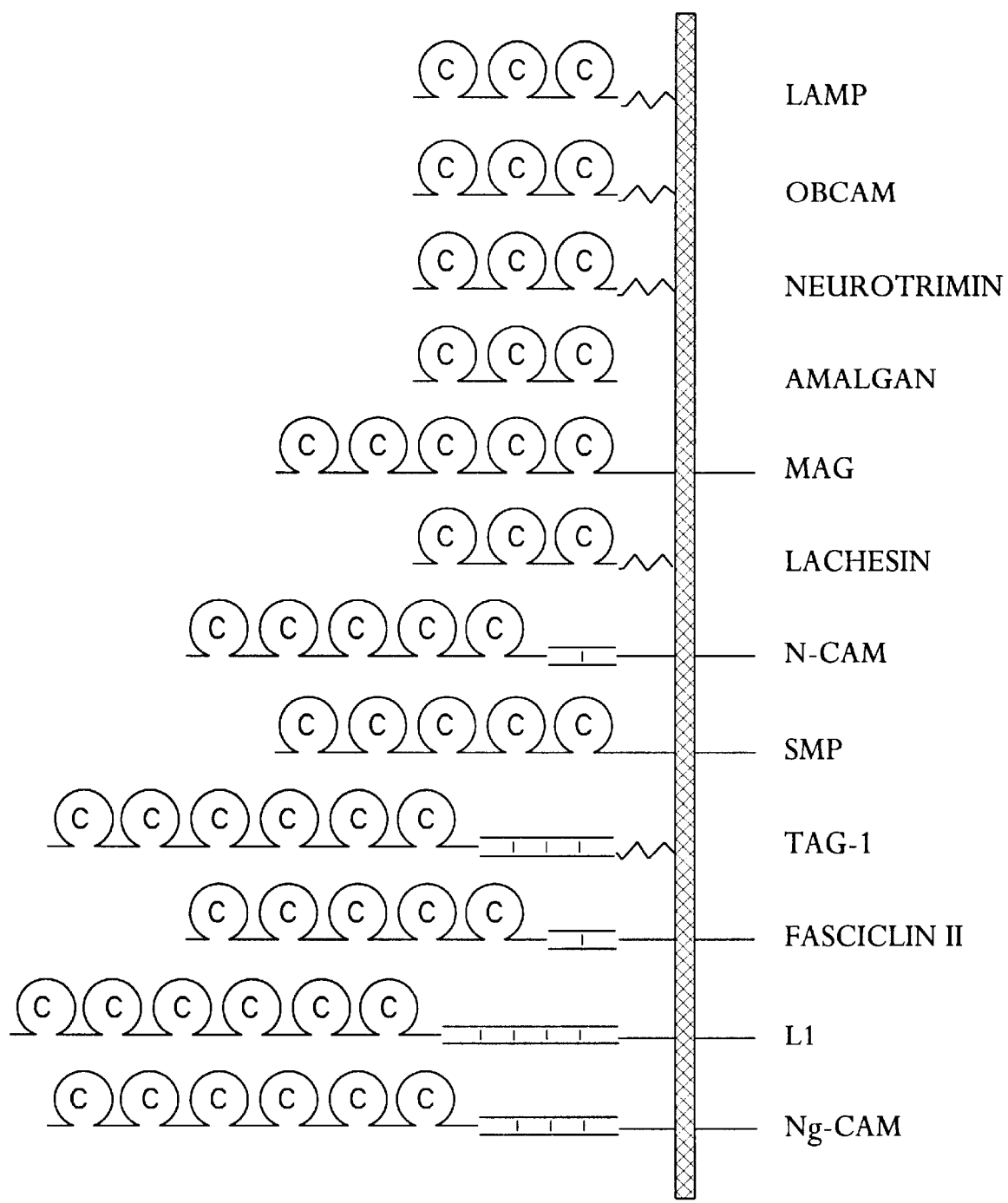
FIG. 2 shows a schematic representation of the immunoglobulin-like material repeats of LAMP and other adhesion molecules.
Figure 4A:
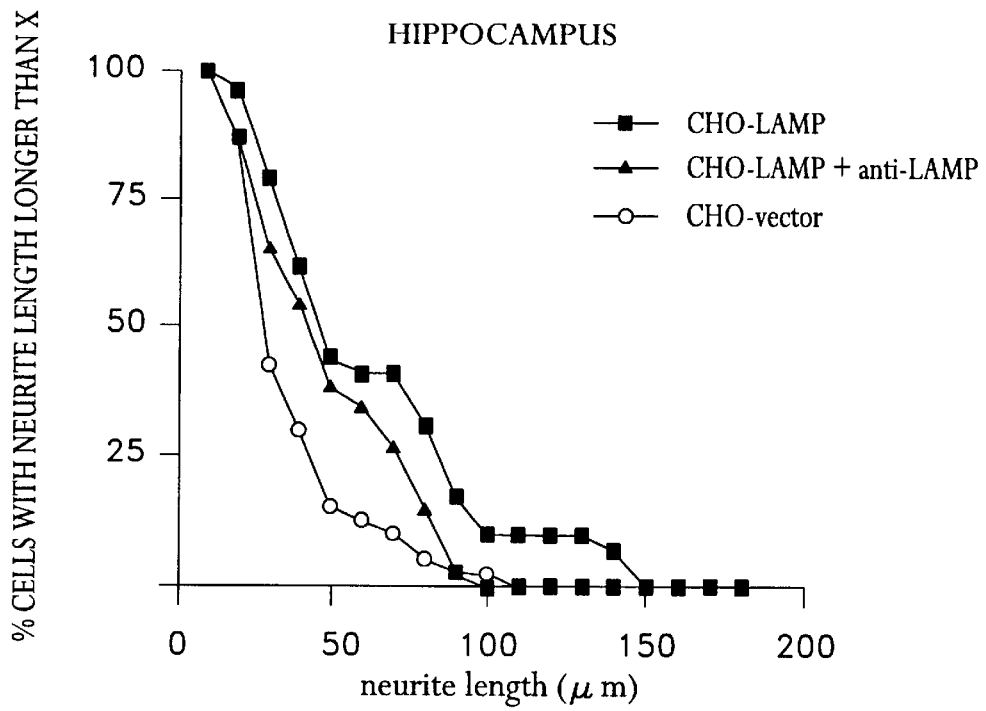
FIGS. 4A–B displays the neurite stimulatory effect of recombinant LAMP expressed at the surface of CHO cells.
Figure 4B:
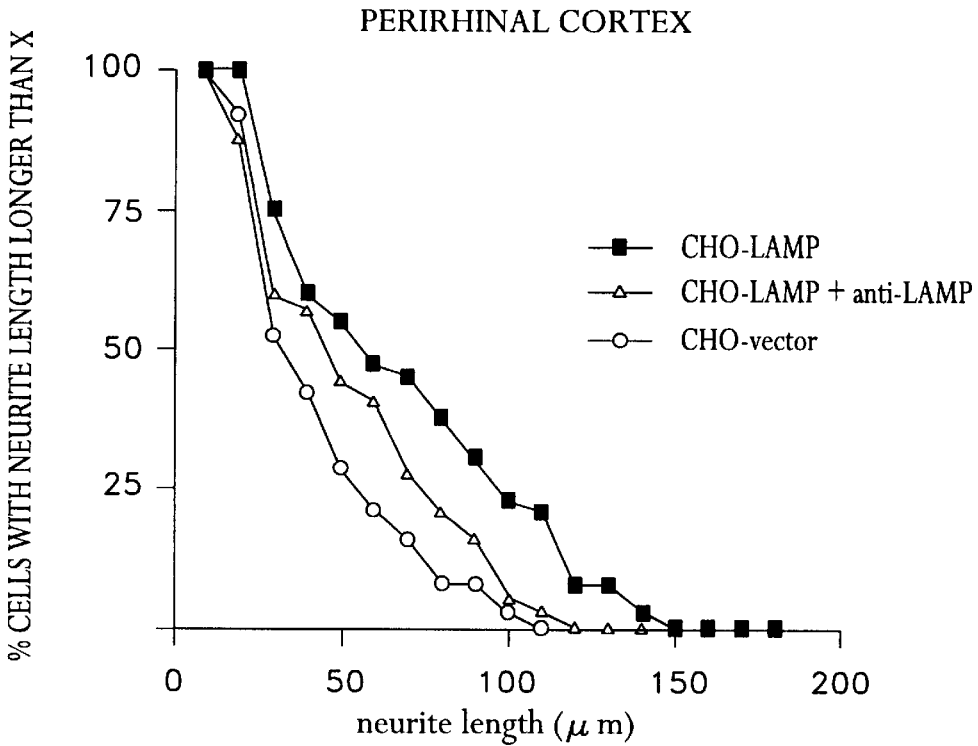
Figure 4C:
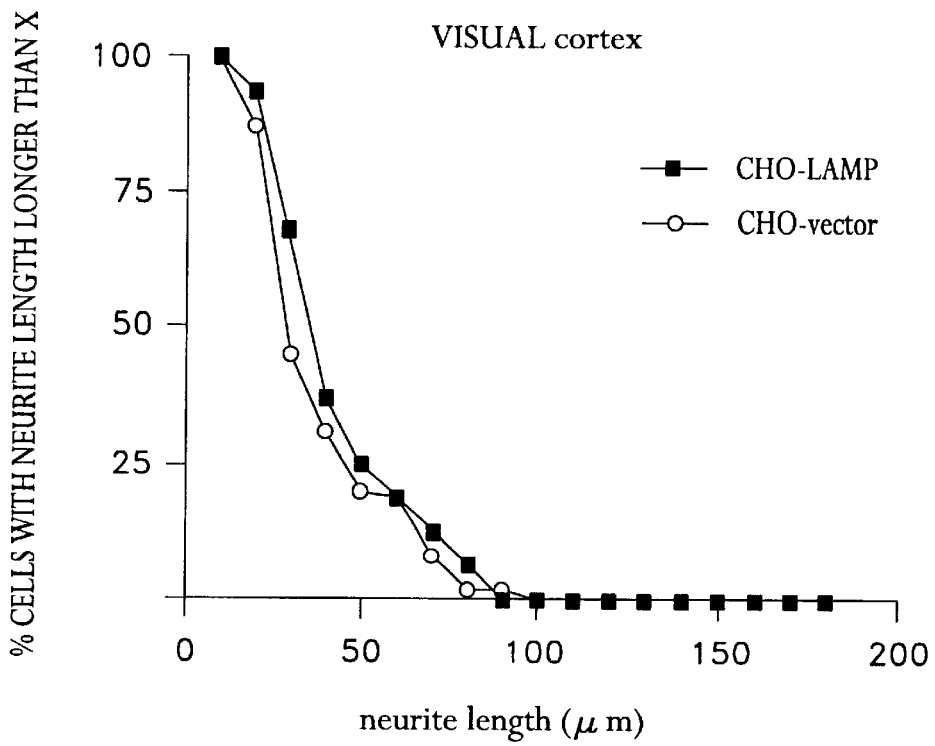
Figure 4D:
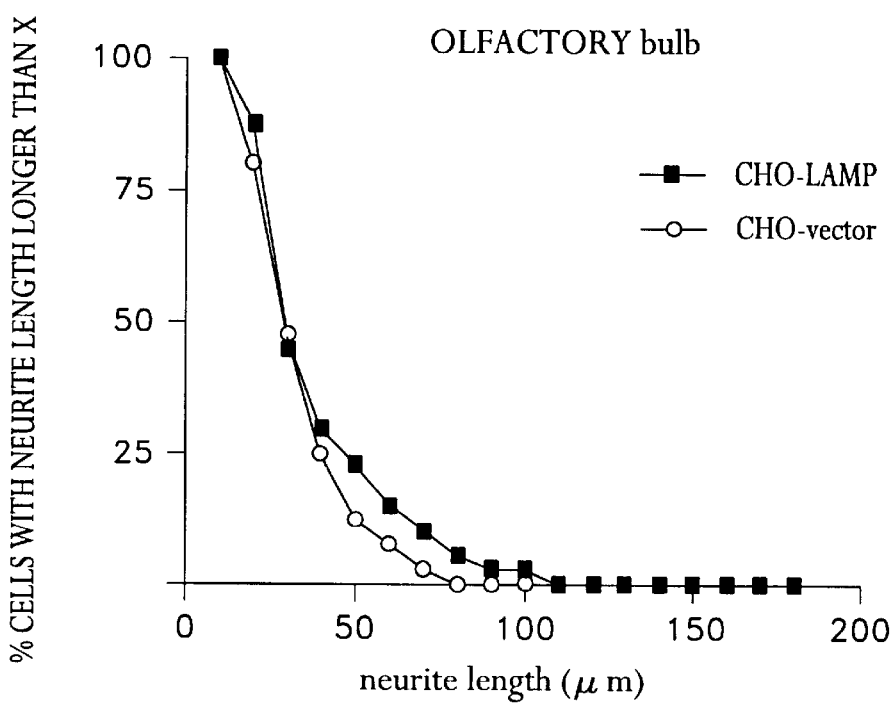

LAMP is homologous with several adhesion molecules in the immunoglobin superfamily as determined by the FASTA computer program described by Pearson and Lipman, *Proc. Natl. Acad. Sci. USA* 85: 2444–2448, 1988, or as determined by manual sequence comparisons. The highest percentages of structural identity, 55% and 54%, respectively, were found with the bovine and rat opioid-binding cell adhesion molecule ("OBCAM") and neurotrimin. The data on these and other sequence homologies are recited below:

| Adhesion molecule | Homolog. residues of Adh. molec. | Homolog. residues of LAMP[12] | Percent identity | Opimiz. score | Z value |
|---|---|---|---|---|---|
| OBCAM[1] | 5–338 | 3–332 | 55.2 | 983 | 94.7 |
| Neurotrimin[2] | | | 54. | | |
| Amalgam[3] | 77–324 | 71–307 | 31.3 | 332 | 9.3 |
| MAG[4] | 234–407 | 126–305 | 30.4 | 221 | 9.5 |
| Lachesin[5] | 14–319 | 17–306 | 29.1 | 342 | 11.0 |
| N-CAM[6] | 260–499 | 86–310 | 27.0 | 282 | 20.0 |
| SMP[7] | 229–404 | 122–303 | 25.7 | 193 | 12.3 |
| TAG-I[8] | 274–505 | 77–305 | 25.5 | 234 | 9.4 |
| FASC-II[9] | 1–317 | 2–305 | 23.9 | 247 | 9.3 |
| L1[10] | 247–500 | 37–294 | 21.3 | 180 | 11.6 |
| Ng-CAM[11] | 405–670 | 16–289 | 21.3 | 140 | 11.9 |

[1]The sequences of the rat and bovine proteins provide essentially the same results. The data from the rat sequence are in the table. The sequences are reported in Schofield et al., EMBO J. 8: 489–495, 1989; Lippman et al., Gene 117: 249–254, 1992.
[2]The sequence is reported in Struyk, et al., J. Neurosci., 15, 2141–2156, 1995. This comparison was done manually.
[3]The sequence is reported in Seeger et al., Cell 55: 589–600, 1988.
[4]The sequence is reported in Arquint et al., Proc. Natl. Acad. Sci. U.S.A. 84: 600–604, 1987; Salzer et al., J Cell Biol 104: 957–965, 1987; and Lai, et al., Proc. Natl. Acad. Sci. 84: 4237–4241, 1987.
[5]The sequence is reported in Karistron et al., Development 118: 509–522, 1993.
[6]The sequences is reported in Cunningham et al., Science 236: 799–806, 1987.
[7]The sequence is reported in Dulac et al., Neuron 8: 323–334, 1992.
[8]The sequence is reported in Furley et al., Cell 61: 157–170, 1990.
[9]The sequence is reported in Grenningloh et al., Cell 67: 45–57, 1991.
[10]The sequence is reported in Moos et al., Nature 334: 701–773, 1988.
[11]The sequence is reported in Burgoon et al., J. Cell Biol. 112: 1017–1029, 1991.
[12]LAMP amino acid positions in this chart and elsewhere in the specification are recited with respect to the rat amino acid sequence set forth at SEQ ID NO:4, which is encoded by the polynucleotide set forth at SEQ ID NO:3 or 7, and/or the human sequence of SEQ ID NO:2 augmented by the rat sequence at the amino and carboxyl ends, as set forth at SEQ ID NO:8.

In the above table, the Z value is indicative of the statistical significance of the homology, with a value of 6 or more indicating probable significance, and a score of 10 or more strongly indicating significance.

The N-terminal of the open reading frame of SEQ ID NOs: 1 and 2 (see FIGS. 1 and 3) has the characteristics of a signal peptide that will be cleared away during protein synthesis. *Nucleic Acids Res.* 14:4683–4690, 1986. This portion of LAMP is represented by the hatched region in FIG. 1. Indeed, microsequencing shows that the N-terminal on processed LAMP is Val$_{29}$. LAMP has a hydrophobic C-terminal sequence consistent with that found on other PI-linked proteins; this kind of sequence is cleaved away when a protein is inserted into a membrane via a PI linkage. See, Cross, *Ann. Rev. Cell Biol.* 6:1–39, 1990; Ferguson and Williams, *Ann. Rev. Biochem.* 57:285–320, 1988; Gerber et al., *J. Biol. Chem.* 267:18168–12173, 1992. This C-terminal portion is represented by the dark, filled region of FIG. 1, with the PI linkage indicated by the "GPI" notation. The C-terminal of processed LAMP is at or near Asn$_{315}$. SEQ ID NO: 7 includes the human cDNA sequence encoding the 29–332 sequence of human LAMP (see, SEQ ID NO:8) while SEQ ID NO: 3 encodes the 29–338 sequence of rat LAMP (see, SEQ ID NO:4). SEQ ID NO: 7 represents the cDNA sequence that encodes the 8–315 amino acid sequence (see, SEQ ID NO:8) of human LAMP, while SEQ ID NO:3 further encodes the 1–315 sequence (see, SEQ ID NO:4) of rat. Further encoded by the cDNA sequence for human and rat respectively, are the 29–315 sequences of LAMP. The minimal LAMP self-binding domain is made up of one or more of the immunoglobulin internal repeats made up of amino acid sequences 46–118, 156–204 and 232–297 of LAMP. The sequence encompassing all of these repeats or "loops", is amino acid residues 46–294 (see, SEQ ID NOs:8 and 4, respectively for human and rat).

The predicted molecular weight of unglycosylated, proteolytically processed LAMP is about 32 kDa. Indeed, in *E. coli* the expression of LAMP cDNA results in protein of apparent molecular weight of 32 kDa (by SDS-PAGE). In Chinese hamster ovary ("CHO") cells, the cDNA produces a protein of apparent molecular weight of 55 kDa, a value intermediate between the unglycosylated molecular weight and molecular weight of the native protein. The extra molecular weight of the CHO-expressed and native proteins is due to glycosylations. Eight sites for N-linked glycosylations (having the sequence Asn-X-Ser/Thr) are found at Asn40, Asn66, Asn136, Asn148, Asn279, Asn287, Asn300, and Asn315. The glycosylation sites are indicated by the balloon symbols in FIG. 1.

As mentioned above, the human and rat sequences of LAMP are highly homologous, sharing 99% sequence identify. The four differences are:

| | RAT | HUMAN |
|---|---|---|
| 1 | Val 55 | Leu 55 |
| 2 | Ala 91 | Ser 91 |
| 3 | Leu 171 | Thr 171 |
| 4 | Phe 332 | Leu 332 |

Accordingly, the invention relates to nucleic acids encoding proteins with 90% homology to human LAMP, preferably 95% homology, more preferably 98% homology, still more preferably 99% homology. In measuring homology, various computer programs may be used including the FASTA program and version 6.0 of the GAP program. The GAP program is available from the University of Wisconsin Genetics Computer Group and utilizes the alignment method of Needleman and Wunsch, *J. Mol. Biol.* 48, 443, 1970, as revised by Smith and Waterman *Adv. Appl. Math.* 2, 482, 1981.

The nucleic acids of the invention can be used as histochemical staining reagents. Such staining can be used to characterize developmental or structural anomalies in biopsy tissue pathology samples. Alternately, such staining can be used to mark a select set of neurons in tissue slides or other preserved specimens for use as anatomical or medical teaching tools.

The nucleic acids of the invention can also be used to transform neural stem cells to program their development as limbic system neurons. These replacement limbic system neurons can be implanted to treat neuropathologies by reconnecting limbic circuits involved in cognition, mood, memory and learning, and cardiovascular regulation, providing therapies for such diseases as dementia, (including without limitation Alzheimer's disease, multi-infarct dementia, dementia associated with Parkinson's disease), all forms of epilepsy, major depression, anxiety (including without limitation manic-depressive illness, generalized anxiety, obsessive-compulsive disorders, panic disorder and others), schizophrenia and schizophrenaform disorders (including without limitation schizoaffecto disorder), cerebral palsy and hypertension.

The nucleic acids of the invention can be used to create LAMP-derived polypeptides that interact with LAMP located at a neuron cell surface to either stimulate the growth and differentiation activities of LAMP or to inhibit these activities. Particularly preferred such polypeptides are soluble LAMP analogs having binding domains effective to bind LAMP. The LAMP-inhibitory polypeptides that are encoded by these nucleic acids can be used to treat diseases characterized by abnormal growth and functioning of limbic neurons, such as epilepsy, Alzheimer's disease and schizophrenia. Antisense strategies to inhibit the expression of LAMP can also be used to treat these diseases.

Another use for the nucleic acids of the invention is to create targeting polypeptides for directing the delivery of biological agents to the limbic system. The polypeptides are useful targeting agents since they bind to LAMP found at the cell surfaces in the limbic system. Such targeting agents can be bound covalently or noncovalently to a biological agent or a vehicle for delivering biological agents. (Biological agents are those that can act on a cell, organ or organism, including, but not limited to, pharmaceutical agents and gene therapy agents.) Numerous targetable delivery vehicles are known, including liposomes, ghost cells and polypeptide matrices. See, for example, Huang et al., *Proc. Natl. Acad. Sci. USA*, 84, 7851–7855, 1987, Kreuter, *Infection* 19 Supp. 4, 224–228, 1991 or Michel et al., *Research in Virology*, 144, 263–267, 1993.

The first embodiment of the invention provides a nucleic acid sequence encoding all or a fragment of LAMP effective to bind to a native LAMP at the cell surface of a neuron. The sequence is preferably derived from the nucleic acid sequence for a LAMP from a mammalian animal, more preferably from a human. Preferably, the sequence comprises a contiguous sequence of at least about 220 nucleotides from SEQ ID NOs: 1 or 4, more preferably, at least about 480 nucleotides, still more preferably, at least about 780 nucleotides. Preferably, the sequence comprises all of one of SEQ ID NOS: 5–18.

The nucleic acid sequence embodiments of the invention are preferably deoxyribonucleic acid sequences, preferably double-stranded deoxyribonucleic acid sequences. However, they can also be ribonucleic acid sequences.

Numerous methods are known to delete sequence from or mutate nucleic acid sequences that encode a protein and to confirm the function of the proteins encoded by these deleted or mutated sequences. Accordingly, the invention also relates to a mutated or deleted version of a LAMP nucleic acid sequence that encodes a protein that retains the ability to bind specifically to a native LAMP bound to a cell surface. The invention also relates to nucleic acids encoding a protein that has the differentiation regulatory activity of LAMP.

As used herein, a "LAMP nucleic acid" means all or part of the LAMP-encoding sequence found in a LAMP-expressing organism, or the complementary strand thereof. "LAMP-encoding nucleic acid" or "nucleic acid sequences for a LAMP" refers to any nucleic acid sequence, whether native or synthetic, that encodes all or part of a LAMP. A "LAMP protein" is a LAMP homologous protein with the ability to bind a native LAMP and possessing the differentiation regulatory activity of a native LAMP. An "animal LAMP" is a LAMP expressed by a member of the animal kingdom. A "LAMP 5' promoter sequence" is a 5' untranscribed region of a gene for a LAMP encoding gene from a LAMP expressing organism that is sufficient to direct transcription in a LAMP-expressing cell.

To construct non-naturally occurring LAMP-encoding nucleic acids, the native sequences can be used as a starting point and modified to suit particular needs. For instance, the sequences can be mutated to incorporate useful restriction sites. See Maniatis et al. *Molecular Cloning, a Laboratory Manual* (Cold Spring Harbor Press, 1989). Such restriction sites can be used to create "cassettes", or regions of nucleic acid sequence that are facilely substituted using restriction enzymes and ligation reactions. The cassettes can be used to substitute synthetic sequences encoding mutated LAMP amino acid sequences. Alternately, the LAMP-encoding sequence can be substantially or fully synthetic. See, for example, Goeddel et al., *Proc. Natl. Acad. Sci. USA*, 76, 106–110, 1979. For recombinant expression purposes, codon usage preferences for the organism in which such a nucleic acid is to be expressed are advantageously considered in designing a synthetic LAMP-encoding nucleic acid.

It will be recognized that many deletional or mutational analogs of nucleic acid sequences for a LAMP will be effective hybridization probes for LAMP-encoding nucleic acid. Accordingly, the invention relates to nucleic acid sequences that hybridize with such LAMP-encoding nucleic acid sequences under stringent conditions. Preferably, the nucleic acid sequence hybridizes with the nucleic acid sequence of one of SEQ ID NOs: 11 or 18 under stringent conditions.

"Stringent conditions" refers to conditions that allow for the hybridization of substantially related nucleic acid sequences. For instance, for a 100 nucleotide sequence, such conditions will generally allow hybridization of sequence with at least about 85% homology, preferably with at least about 90% homology. Such hybridization conditions are described by Sambrook et al., *Molecular Cloning: A Laboratory Manual*, 2nd ed., Cold Spring Harbor Press, 1989.

Nucleic acid molecules that will hybridize to a LAMP-encoding nucleic acid under stringent conditions can be identified functionally, using methods outlined above, or by using the hybridization rules reviewed in Sambrook et al., *Molecular Cloning: A Laboratory Manual*, 2nd ed., Cold Spring Harbor Press, 1989.

Without limitation, examples of the uses for hybridization probes include: the histochemical uses described above; measuring mRNA levels, for instance, to identify a sample's tissue type or to identify cells that express abnormal levels of LAMP; and detecting polymorphisms in the LAMP gene. RNA hybridization procedures are described in Maniatis et al. *Molecular Cloning, a Laboratory Manual* (Cold Spring Harbor Press, 1989).

Rules for designing polymerase chain reaction ("PCR") primers are now established, as reviewed by *PCR Protocols*, Cold Spring Harbor Press, 1991. Degenerate primers, i.e., preparations of primers that are heterogeneous at given sequence locations, can be designed to amplify nucleic acid sequences that are highly related to, but not identical to, a LAMP nucleic acid. For instance, such degenerate primers can be designed from the human LAMP cDNA and used to amplify nucleic acid sequences for LAMPs from non-human species, as illustrated in the examples.

As discussed above, deletional or mutational methods of producing recombinant proteins that retain a given activity are well known. Thus, the embodiments of the present invention that relate to proteins also encompass analogs of LAMP that retain the ability to bind to native LAMP expressed at a cell surface. These analogs preferably lack no more than about 45 amino acid residues of deleted sequence at the N-terminal end, more preferably no more than about 37 amino acid residues. At the C-terminal, the analogs preferably lack no more than about 44 amino acid residues of deleted sequence, more preferably no more than about 34 amino acid residues. The remaining LAMP protein sequence will preferably have no more than about 10 point mutations, preferably no more than about 5 point mutations, more preferably no more than about 3 point mutations. The point mutations are preferably conservative point mutations. Preferably, the analogs will have at least about 90% homology, preferably at least about 95%, more preferably at least about 98%, still more preferably at least about 99%, to any of the proteins of one of SEQ ID NOs.: 1–18, preferably of SEQ ID NOs: 11–18.

Mutational and deletional approaches can be applied to all of the nucleic acid sequences of the invention that express LAMP proteins. As discussed above, conservative mutations are preferred. Such conservative mutations include mutations that switch one amino acid for another within one of the following groups:

1. Small aliphatic, nonpolar or slightly polar residues: Ala, Ser, Thr, Pro and Gly;
2. Polar, negatively charged residues and their amides: Asp, Asn, Glu and Gln;
3. Polar, positively charged residues: His, Arg and Lys;
4. Large aliphatic, nonpolar residues: Met, Leu, Ile, Val and Cys; and
5. Aromatic residues: Phe, Tyr and Trp.

A preferred listing of conservative substitutions is the following:

| Original Residue | Substitution |
| --- | --- |
| Ala | Gly, Ser |
| Arg | Lys |
| Asn | Gln, His |
| Asp | Glu |
| Cys | Ser |
| Gln | Asn |
| Glu | Asp |
| Gly | Ala, Pro |
| His | Asn, Gln |
| Ile | Leu, Val |
| Leu | Ile, Val |
| Lys | Arg, Gln, Glu |
| Met | Leu, Tyr, Ile |
| Phe | Met, Leu, Tyr |
| Ser | Thr |
| Thr | Ser |
| Trp | Tyr |
| Tyr | Trp, Phe |
| Val | Ile, Leu |

The types of substitutions selected may be based on the analysis of the frequencies of amino acid substitutions between homologous proteins of different species developed by Schulz et al., *Principles of Protein Structure*, Springer-Verlag, 1978, on the analyses of structure-forming potentials developed by Chou and Fasman, *Biochemistry* 13, 211, 1974 and Adv. Enzymol, 47, 45–149, 1978, and on the analysis of hydrophobicity patterns in proteins developed by Eisenberg et al., *Proc. Natl. Acad. Sci. USA* 81, 140–144, 1984; Kyte & Doolittle; *J. Molec. Biol.* 157, 105–132, 1981, and Goldman et al., *Ann. Rev. Biophys. Chem.* 15, 321–353, 1986. All of these references are incorporated herein in their entirety by reference.

Since, the four identified substitutions between rat and human LAMP are clearly functionally acceptable, the invention provides LAMP proteins having any combination of these substitutions.

As discussed above, at least one of the immunoglobin-like internal repeats of LAMP is the minimal LAMP self-binding domain, i.e., the minimal amino acid sequence needed to specifically interact with LAMP. Additional LAMP-related sequence may serve to enhance this self-binding activity. The exact boundaries of the minimal self-binding domain and the adjacent sequence that improves the efficiency of the minimal sequence can be determined by gene expression methods well known to the art. For instance, the nucleic acid for the minimal sequence can be inserted at a downstream portion of the gene for a cell-surface protein and the recombinant gene expressed as a cell-surface fusion protein. The ability of the fusion protein to interact with LAMP can be tested, for instance, by one of the methods outlined in the Examples.

The invention also provides for the LAMP or LAMP-related proteins having LAMP self-binding activity encoded by any of the nucleic acids of the invention in a purity of at least about 95% with respect to macromolecules, preferably 98%, more preferably 99%. The purities are achieved, for example, by applying protein purification methods, such as those described below, to the culture medium or lysate of a recombinant cell according to the invention.

The invention further provides isolated LAMP or analogs of LAMP, with the proviso that they are not rat or bovine LAMP. The LAMP or analog of LAMP preferably comprises a sequence that is homologous to a 73 amino acid stretch of the sequence of an animal LAMP, more preferably a 159 amino acid stretch, still more preferably a 252 amino acid stretch. The LAMP or analog of LAMP preferably comprises one, two or three of the immunoglobulin-like repeats. The LAMP or LAMP analog protein is preferably at least about 90%, preferably about 95%, more preferably 98%, still more preferably about 99% homologous to the corresponding sequence of an animal LAMP. The protein has at least about 2, preferably about 3, more preferably about 4, amino acid substitutions relative to the 29 to 315 amino acid sequence of rat LAMP, where "substitutions" includes deletions. In a preferred embodiment, the protein has at least about 10, preferably 20, more preferably 40, yet more preferably 80 substitutions relative to rat or bovine LAMP and comprises at least one of the immunoglobulin-like repeats of LAMP, preferably the third repeat (amino acids 232 to 297 of rat LAMP).

The invention further provides antigens comprising the proteins of the above paragraph. These antigens can be used to produce antibodies with specificities that, for instance, differ from the specificity of antibodies against rat LAMP.

The methods by which the LAMP analogs of the above praragraphs, which include deletional and mutational analogs, are discussed above with respect to LAMP or LAMP analog nucleic acids. These nucleic acids can be used to create organisms or cells that produce LAMP or LAMP analogs. Purification methods, including facilitative molecular biology methods, are described below.

One simplified method of isolating polypeptides synthesized by an organism under the direction of one of the nucleic acids of the invention is to recombinantly express a fusion protein wherein the fusion partner is facilely affinity purified. For instance, the fusion partner can be glutathione s-transferase, which is available on commercial expression vectors (e.g., vector pGEX4T3, available from Pharmacia, Uppsala, Sweden). The fusion protein can then be purified on a glutathione affinity column (for instance, that available from Pharmacia). Of course, the recombinant polypeptides can be affinity purified without such a fusion partner using the 2G9 antibody, as described in Zacco et al., *J. Neuroscience* 10, 73–90, 1990 or another LAMP-specific antibody or previously purified LAMP, which has self-adhesion activity. If fusion proteins are used, the fusion partner can be removed by partial proteolytic digestion approaches that preferentially attack unstructured regions such as the linkers between the fusion partner and LAMP. The linkers can be designed to lack structure, for instance using the rules for secondary structure forming potential developed, for instance, by Chou and Fasman, *Biochemistry* 13, 211, 1974 and Chou and Fasman, *Adv. in Enzymol.* 47, 45–147, 1978. The linker can also be designed to incorporate protease target amino acids, such as, for trypsin, arginine and lysine residues. To create the linkers, standard synthetic approaches for making oligonucleotides may be employed together with standard subcloning methodologies. Other fusion partners besides GST may be used. Procedures that utilize eukaryotic cells, particularly mammalian cells, are preferred since these cells will post-translationally modify the protein to create molecules highly similar to or functionally identical to native proteins.

Additional purifications techniques can be applied, including without limitation, preparative electrophoresis, FPLC (Pharmacia, Uppsala, Sweden), HPLC (e.g., using gel filtration, reverse-phase or mildly hydrophobic columns), gel filtration, differential precipitation (for instance, "salting out" precipitations), ion-exchange chromatography and affinity chromatography.

A protein or nucleic acid is "isolated" in accordance with the invention if it is substantially purified. Preferably, the protein or nucleic acid is at least 60% pure with respect to macromolecules, more preferably 80% pure, still more preferably 90% pure, yet more preferably 95% pure, yet still more preferably 99% pure.

One aspect of the present invention is directed to the use of "antisense" nucleic acid to treat neurological diseases, including epilepsy. The approach involves the use of an antisense molecule designed to bind nascent mRNA (or "sense" strand) for a LAMP, thereby stopping or inhibiting the translation of the mRNA, or to bind to the LAMP gene to interfere with its transcription. For discussion of the design of nucleotide sequences that bind genomic DNA to interfere with transcription, see Helene, *Anti-Cancer Drug Design* 6, 569, 1991. Once the sequence of the mRNA sought to be bound is known, an antisense molecule can be designed that binds the sense strand by the Watson-Crick base-pairing rules, forming a duplex structure analogous to the DNA double helix. *Gene Regulation: Biology of Antisense RNA and DNA*, Erikson and Ixzant, eds., Raven Press, New York, 1991; Helene, *Anti-Cancer Drug Design*, 6:569 (1991); Crooke, *Anti-Cancer Drug Design* 6, 609, 1991.

A serious barrier to fully exploiting this antisense technology is the problem of efficiently introducing into cells a sufficient number of antisense molecules to effectively interfere with the translation of the targeted mRNA or,the function of DNA. One method that has been employed to overcome this problem is to covalently modify the 5' or the 3' end of the antisense polynucleic acid molecule with hydrophobic substituents. These modified nucleic acids generally gain access to the cells interior with greater efficiency. See, for example, Boutorin et al., *FEBS Lett.* 23,1382–1390, 1989; Shea et al, *Nucleic Acids Res.* 18, 3777–3783, 1990. Additionally, the phosphate backbone of the antisense molecules has been modified to remove the negative charge (see, for example, Agris et al., *Biochemistry* 25, 6268, 1986; Cazenave and Helene in *Antisense Nucleic Acids and Proteins: Fundamentals and Applications*, Mol and Van der Krol, eds., p. 47 et seq., Marcel Dekker, New York, 1991) or the purine or pyrimidine bases have been modified (see, for example, *Antisense Nucleic Acids and Proteins: Fundamentals and Applications*, Mol and Van der Krol, eds., p. 47 et seq., Marcel Dekker, New York, 1991; Milligan et al. in *Gene Therapy For Neoplastic Diseases*, Huber and Laso, eds., p. 228 et seq., New York Academy of Sciences, New York, 1994). Other methods to overcome the cell penetration barrier include incorporating the antisense polynucleic acid sequence into an expression vector that can be inserted into the cell in low copy number, but which, when in the cell, can direct the cellular machinery to synthesize more substantial amounts of antisense polynucleic molecules. See, for example, Farhood et al., *Ann. N.Y. Acad. Sci.* 716, 23, 1994. This strategy includes the use of recombinant viruses that have an expression site into which the antisense sequence has been incorporated. See, e.g., Boris-Lawrie and Temin, *Ann. N.Y. Acad. Sci.,* 716:59 (1994). Others have tried to increase membrane permeability by neutralizing the negative charges on antisense molecules or other nucleic acid molecules with polycations. See, e.g. Wu and Wu, *Biochemistry,* 27:887–892, 1988; Behr et al., *Proc. Natl. Acad Sci U.S.A.* 86:6982–6986, 1989.

The invention also encompasses the use of gene therapy approaches to insert a gene (1) expressing a LAMP protein into de-differentiated limbic system-derived tumor cells or into stem cells, (2) expressing a LAMP-directed anti-sense molecule, or (3) a limbic system-targeted gene functionally linked to a LAMP promoter.

For gene therapy, medical workers try to incorporate, into one or more cell types of an organism, a DNA vector capable of directing the synthesis of a protein missing from the cell or useful to the cell or organism when expressed in greater amounts. The methods for introducing DNA to cause a cell to produce a new protein or a greater amount of a protein are called "transfection" methods. See, generally, Neoplastic Diseases, Huber and Lazo, eds., New York Academy of Science, New York, 1994; Feigner, *Adv. Drug Deliv. Rev.,* 5:163 (1990); McLachlin, et al., *Progr. Nucl. Acids Res. Mol. Biol.,* 38:91 (1990); Karlsson, S. *Blood,* 78:2481 (1991); Einerhand and Valerio, *Curr. Top. Microbiol. Immunol.,* 177:217–235 (1992); Makdisi et al., *Prog. Liver Dis.,* 10:1 (1992); Litzinger and Huang, *Biochim. Biophys. Acta,* 1113:201 (1992); Morsy et al., *J.A.M.A.,* 270:2338 (1993); Dorudi et al., *British J. Surgery,* 80:566 (1993).

A number of the above-discussed methods of enhancing cell penetration by antisense nucleic acid are generally applicable methods of incorporating a variety of nucleic acids into cells. Other general methods include calcium phosphate precipitation of nucleic acid and incubation with the target cells (Graham and Van der Eb, *Virology,* 52:456, 1983), co-incubation of nucleic acid, DEAE-dextran and cells (Sompayrac and Danna, *Proc. Natl. Acad. Sci.,* 12:7575, 1981), electroporation of cells in the presence of nucleic acid (Potter et al., *Proc. Natl. Acad. Sci.,* 81:7161–7165, 1984), incorporating nucleic acid into virus coats to create transfection vehicles (Gitman et al., *Proc. Natl. Acad. Sci. U.S.A.,* 82:7309–7313, 1985) and incubating cells with nucleic acid incorporated into liposomes (Wang and Huang, *Proc. Natl. Acad. Sci.*, 84:7851–7855, 1987). One approach to gene therapy is to incorporate the gene sought to be introduced into the cell into a virus, such as a herpes virus, adenovirus, parvovirus or a retrovirus. See, for instance, Akli et al., *Nature Genetics* 3, 224, 1993.

The nucleic acid compositions of the invention, including antisense and gene therapy compositions, can be administered orally, topically, rectally, nasally, vaginally, by inhalation, for example by use of an aerosol, or parenterally, i.e. intramuscularly, subcutaneously, intraperitoneallly, intraventrucularly, intraventricularly, or intravenously. The polynucleotide compositions can be administered alone, or it can be combined with a pharmaceutically-acceptable carrier or excipient according to standard pharmaceutical practice. For the oral mode of administration, the polynucleotide compositions can be used in the form of tablets, capsules, lozenges, troches, powders, syrups, elixirs, aqueous solutions and suspensions, and the like. In the case of tablets, carriers that can be used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the polynucleotide compositions can be combined with emulsifying and suspending agents. If desired, certain sweetening and/or flavoring agents can be added. For parenteral administration, sterile solutions of the conjugate are usually prepared, and the pH of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. For pulmonary administration, diluents and/or carriers will be selected to be appropriate to allow the formation of an aerosol.

Generally, the polynucleotide compositions will be administered in an effective amount. An effective amount is an amount effective to either (1) reduce the symptoms of the disease sought to be treated or (2) induce a pharmacological change relevant to treating or preventing the disease sought to be treated.

For viral gene therapy vectors, dosages will generally be from about 1 μg to about 1 mg of nucleic acid per kg of body mass. For non-infective gene therapy vectors, dosages will generally be from about 1 μg to about 100 mg of nucleic acid per kg of body mass. Antisense oligonucleotide dosages will generally be from about 1 μg to about 100 mg of nucleic acid per kg of body mass.

The stem cells that are useful in neural stem cell replacement therapy include human cortical and subcortical fetal brain cells, porcine fetal brain cells, human subventricular zone cells and glial progenitor cells, including O2A cells (which are progenitors for all glial cell types, including astrocytes and oligodendrocytes).

The biological agents that can be usefully targeted to the limbic system include, without limitation neurotransmitter biosynthetic enzymes (such as tyrosine hydroxylase), neurotransmitter transporters (such as the GABA transporter), neurotransmitter receptors (such as type Ia, Ib, II or III dopamine receptors, α and β adrenergic receptors and 5-HT receptors), neurotrophic and growth factors (such NGF, BDNF, NT-3,4,5, TGFβ, basic FGF and GDNF) neurotrophic factor receptors, protein kinases (such as MAP kinases and protein kinase C) and protein phosphatases. Further agents include, without limitation, antidepressants, neuroleptics, anti-epileptics and antagonists of neurotransmitter receptors (such as type Ia, Ib, II or III dopamine receptors, α and β adrenergic receptors and 5-HT receptors). Such agents include antisense therapeutic agents including antisense gene therapy agents.

LAMP promoter, meaning promoters linked to LAMP nucleic acid in the genome of an animal that is sufficient to confer limbic system-specific expression, in addition to the promoter defined in SEQ ID NO: 20, can be isolated by probing a genomic library with one of the LAMP nucleic acids of the invention. See, Maniatis et al., *Molecular Cloning*, Cold Spring Harbor Press, 1989. The ability of the promoter to confer cell-specific expression confirmed by transfection experiments and experiments that create transgenic animals. Id. The invention relates to such LAMP promoters and mutated analogs that retain cell-type specific function.

5' LAMP promoter sequences can be isolated using a genomic library containing relatively short inserts appropriate for PCR amplification. This library is made by first digesting genomic DNA with a relatively non-specific restriction endonuclease, such as one that recognizes a 4–6 base pair ("bp") sequence, or by shearing genomic DNA until relatively short (e.g. 1000–3000 bp) fragments are obtained. The genomic fragments are subcloned into a vector. The vector DNA is PCR amplified with a first vector-based primer that primes DNA synthesis towards the insert site and a second primer, based on the 5' sequence of SEQ ID NO: 1 or SEQ ID NO: 2, that primes DNA synthesis in the 5' direction. In this way, a LAMP promoter sequence is rapidly synthesized.

The promoter sequences of the invention include all sequences within 200 base pairs of the transcription start site that affect the efficiency with which LAMP is transcribed. Preferably, the promoter will contain sufficient sequence to confer neural-specific transcription, still more preferably, limbic system-specific expression. Included in such promoter sequence is the first intron of the LAMP gene, the sequence of which, for mouse LAMP, is made up of nucleotides 1033 through 1851 in SEQ ID NO: 20. This intron, shown in FIG. 5, has a consensus binding sites for the Hox-1.3 and AP-1 transcription factors (beginning at nucleotides 1,312 and 1,282, respectively) and a TATA box consensus sequence (centered at about nucleotide 1,821). The first 350 nucleotides of the 5' portion of the promoter has CREB, AP-1, SP-1 and TATA consensus sequences beginning at nucleotides 313, 359, 524 and 617, respectively (or, relative to the start of transcription, at −340, −294, −129 and −36, respectively). The preferred embodiment comprises a sequence that is homologous to the −647 to −1 portion of a LAMP promoter, more preferably the −350 to −1 portion, yet more preferably the −130 to −1 protion. The −647 to −1, −350 to −1 or −130 to −1 promoter sequence will preferably have at least about 60% homology sequence of a LAMP promoter, more preferably at least about 70%, yet more preferably 80%, still more preferably at least about 90%. An example of such a sequence, derived from mouse genomic DNA, is represented in FIG. 5, where the arrow represents the dominant transcription start site. (+1).

The gene therapy agents that can usefully be targeted to the limbic system include, without limitation, genes or antisense therapeutics for protein kinases (such as, without limitation, protein kinase C), enzymes including neurotransmitter biosynthesizing enzymes (such as, without limitation, acetylcholine synthesizing enzymes), neurotransmitter transporters, neurotrophins (i.e., factors that provide neural cells with nutritive support) and growth factors (such as, without limitation, NGF, BDNF, NT-3,4,5, TGFβ, basic FGF and GDNF), ion channels (such as, without limitation, calcium and sodium channels), neurotransmitter receptors (such as, without limitation, dopamine receptors), neurotrophic factor and receptors (such as NGF, β-DNF, NT-3, 4,5, TGFβ, basic FGF and GDNF) neurotrophic factor receptors, protein kinases (such as MAP kinases and protein kinase C) and protein phosphatases. In Alzheimer's, genes or acetyl choline synthesis will aide to replace diminished acetylcholine levels in he limbic system. Genes for growth factors and neurotrophic factors will help keep neurons from succumbing to neurodegenerative diseases that affect the limbic system.

The invention also provides a useful marker protein to examine the genome of families with genetic disorders to determine whether the affected members share a polymorphism at or adjacent to the LAMP gene. To identify polymorphisms, several techniques are used, including without limitation examining for variable number tandem repeats in the DNA at or adjacent to the LAMP gene, probing for restriction length polymorphisms, probing for variations in the length of PCR-amplified fragments, and examining the nucleotide sequence at or near the LAMP. These and other methods are described in the text by Victor McKusak, *Mandelian Inheritance in Man: A Catalog of Human Genes and Genetic Disorders,* 11th edition, Johns Hopkins University Press, 1994, and in a series entitled Genes edited by B. Lewin and published by Wiley & Sons. PCR methods are usefully employed for examining sequence information. In connection with this aspect of the invention, "probing" shall mean examining genomic DNA for any useful indicator of a polymorphism.

The invention also relates to methods of measuring a LAMP mRNA from a tissue or staining a tissue for a LAMP mRNA. Useful methods of measuring mRNA include Southern blot analysis, dot blot analysis, nuclear transcription analysis, histochemical staining for mRNA and polymerase chain reaction amplification methods. See generally, Ausubel et al., *Current Protocols in Molecular Biology,* Wiley Press, 1993; *PCR Protocols,* Cold Spring Harbor Press, 1991; and Sambrook et al., *Molecular Cloning: A Laboratory Manual,* 2nd ed., Cold Spring Harbor Press, 1989. For in-situ nucleic acid hybridization techniques, see Baldino et al., *Methods in Enzymology* 168, 761–777, 1989; Meson et al., *Methods in Enzymology* 168, 753–761, 1989; Harper et al., *Methods in Enzymology.* 151, 539–551, 1987; Angerer et al., *Methods in Enzymology* 152, 649–661, 1987; Wilcox et al., *Methods in Enzymology* 124, 510–533, 1986. Methods of assessing mRNA amounts are useful in diagnosing abnormalities associated with epilepsy and schizophrenia. For these uses, biopsy tissue and CSF fluid can be usefully assayed.

PCR methods of amplifying nucleic acid will utilize at least two primers. One of these primers will be capable of hybridizing to a first strand of the nucleic acid to be amplified and of priming enzyme-driven nucleic acid synthesis in a first direction. The other will be capable of hybridizing the reciprocal sequence of the first strand (if the sequence to be amplified is single stranded, this sequence will initially be hypothetical, but will be synthesized in the first amplification cycle) and of priming nucleic acid synthesis from that strand in the direction opposite the first direction and towards the site of hybridization for the first primer. Conditions for conducting such amplifications, particularly under preferred stringent conditions, are well known. See, for example, *PCR Protocols,* Cold Spring Harbor Press, 1991. Appropriate nucleic acid primers can be ligated to the nucleic acid sought to be amplified to provide the hybridization partner for one of the primers. In this way, only one of the primers need be based on the sequence of the nucleic acid sought to be amplified.

The samples that can be assayed or stained for nucleic acid encoding LAMP include, without limitation, cells or tissues (including nerve tissues), protein extracts, nucleic acid extracts and biological fluids such as cerebra fluid, serum and plasma. Preferred samples are nervous system-derived samples.

All treatment methods of the invention are applicable to animals in general, although mammals—particularly humans—are preferred treatment subjects.

The invention is described in more detail, but without limitation, by reference to the examples set forth below.

EXAMPLE 1

Isolation of Rat LAMP cDNA

LAMP was purified from adult rat hippocampal membranes as described by Zacco et al., *J. Neurosci.* 10: 73–90, 1990, using the 269 antibody as an affinity reagent. The purified protein was electrophoresed by SDS-PAGE and electroblotted onto a PVDF membrane in preparation for microsequencing as described by Matsudaira, *J. Bio. Chem.* 262: 10035–10038,1987. The electroblotted LAMP was sequenced on an Applied Biosystems 470A gas phase sequencer equipped with a 120A on-line PTH analyzer as described by Henzel et al., *J. Chromatogr.* 404: 41–52, 1987. The N-terminal sequence was determined to be VRSVD-FNRGTDNITVROGDTA (SEQ ID NO:9), using the single letter amino acid abbreviations.

The sequences DFNRGTD (SEQ ID NO:10) and ITVRQGD (SEQ ID NO:11), both found in the N-terminal sequence, were used to design two separate batches of redundant oligonucleotide hybridization probes. The batches were as follows:

Group 1:
GAYTYAAYCGIGGIACIGAY (SEQ ID NO:12)
GAYTTYAAYAGRGGIACIGAY (SEQ ID NO:13)
Group 2:
ATHACIGTICGICARGGIGAY (SEQ ID NO:14)
ATHACIGTIAGRCARGGIGAY (SEQ ID NO:15)
where R=A/G, Y=C/T, I=Inosine and H=A/C/T. These probes were end-labeled with $^{32}P$ and used to screen an adult rat hippocampus cDNA library cloned in λgt11 (Clontech, Palo Alto, Calif.). The methodology was as described by Maniatis, *Molecular Cloning: A Laboratory Manual,* Cold Spring Harbor Press, 1989 and Hockfield et al., *Molecular Probes of the Nervous System,* Cold Spring Harbor Press, 1994, as was all the methodology of the Examples, unless otherwise specified. The insert DNA from lambda plaques that were positive for both probes was amplified by PCR using the λgt11 forward and reverse primers available from Promega (Madison, Wis.). Amplified inserts were subcloned into pCR II (Invitrogen, San Diego, Calif.) and sequenced by the dideoxy chain termination method. Sanger et al., *Proc. Natl. Acad. Sci. USA* 74: 5463–5467, 1977. Four identical cDNA inserts had the sequence of SEQ ID NO: 2.

EXAMPLE 2

Human LAMP cDNA

The following PCR primer pairs were designed based on the sequence of the rat LAMP cDNA of FIG. 3 and were used to amplify human cerebral cDNAs of the sizes indicated in the parentheses below:

| Pair H-1 | Primer 1: GAYTTYAAYCGIGGIACIGAY (SEQ ID NO: 16)<br>Primer 2: TGCCAGCAGCCACAGTGGTA (SEQ ID NO: 17)<br>(Size of the sequence amplified: 888 bp.) | nt 152–172<br>nt 1020–1039 |
|---|---|---|
| Pair H-2 | Primer 1: CGAATCCAGAAGGTGGATGT (SEQ ID NO: 18)<br>Primer 2: TGCCAGCAGCCACAGTGGTA (SEQ ID NO: 19)<br>(Size of the sequence amplified: 696 bp.) | nt 344–363<br>nt 1020–1039 |
| Pair H-3 | Primer 1: CGAATCCAGAAGGTGGATGT (SEQ ID NO: 20)<br>Primer 2: GTAGTGTTCCTCAGTGACGT (SEQ ID NO: 21)<br>(Size of sequence amplified 566 bp.) | nt 344–363<br>nt 891–910 |
| Pair H-9 | Primer 1: CGGAATTCATGGTCGGGAGAGTTCAACC (SEQ ID NO: 22)<br>Primer 2: GTAGTGTTCCTCAGTGACGT (SEQ ID NO: 23)<br>(Size of the sequence amplified: 854 bp.) | nt 56–75<br>nt 891–910 |
| Pair H-8 | Primer 1: CGGAATTCATGGTCGGGAGAGTTCAACC (SEQ ID NO: 24)<br>Primer 2: TCAACCAGGCCACTTTCGAG (SEQ ID NO: 25)<br>(Size of the sequence amplified: 195 bp.) | nt 56–75<br>nt 232–251 |
| Pair H-5 | Primer 1: TCTAAGAGCAATGAAGCCAC (SEQ ID NO: 26)<br>Primer 2: TTAACATTTGCTGAGAAGGC (SEQ ID NO: 27)<br>(Size of the sequence amplified: 347 bp.) | nt 725–744<br>nt 1053–1072 |

The sequences amplified from human cerebral cortex cDNA by these primers were cloned into pCR II (Invitrogen, San Diego, Calif.) or pGEM T (Promega, Madison, Wis.). The inserts were sequenced by the chain termination method and the assembled sequence designated SEQ ID NO: 1 (see FIG. 3). The amplified regions are indicated in FIG. 1.

EXAMPLE 3

Northern Blot Analysis of LAMP Expression

Total cellular RNA was isolated from various tissues of adult, Sprague-Dawley rats and the poly-adenylated fraction was isolated therefrom using the PolyATract™ isolation system (Promega, Madison, Wis.). For each tissue-type, 3 µg of poly(A)+ RNA was separated on an agarose-formaldehyde gel, transferred to a nylon membrane (Nytran™, Schleicher & Schuel, Keene, NH), UV cross-linked and hybridized overnight under stringent conditions with one of the $^{32}$P probes described below. The first probe was an RNA transcript, produced with T7 RNA polymerase, of a pCR II vector containing the rat cDNA insert that had been linearized with Bal I. This process produced a probe of the 519–1238 sequence of FIG. 3 (rat). A sense control probe was prepared with SP6 RNA polymerase acting on a Nar I-digested rat LAMP PCRII template (Nt. 1-527 of FIG. 3). An 53 base oligonucleotide probe corresponding to nucleotides 973–1025 of SEQ ID NO: 2 was labelled by adding a $^{32}$P poly(A) tail.

The first LAMP probe identified a 1.6 and a 8.0 kb transcript in Hippocampus, perirhinal cortex and cerebellum, but identified no transcripts in kidney, lung or liver. The oligonucleotide probe, derived from a region with little homology with OBCAM, also hybridized with the 1.6 and 8.0 kb transcripts.

EXAMPLE 4

Histochemistry

For these studies, the 53 base oligonucleotide probe was labelled with an $^{35}$S poly(A) tail. Tissue slices, fixed with 4% formaldehyde, were hybridized with the probe at 58° C., at a probe concentration of $10^6$ cpm/ml in hybridization buffer (50% formamide, 10% dextran sulfate, 0.2 M NaCl, 1×Denhardt's solution, 10 mM Tris, 1 mM EDTA, pH 8.0).

Stringent condition post-hybridization washes included 1 hour in 1×SSC at 60° C. A control 53 base oligonucleotide probe, comprising the sequence complementary to the primary probe, was used on corresponding control tissue slices, but produced no signal. Signal was detected by autoradiography.

In a coronal section through the forebrain from a day E16 of a rat embryo shows intense hybridization in the limbic perirhinal cortical region (pr) and hypothalamus (hy), and a small signal over background in the non-limbic dorsal sensorimotor cortex. A section from day E20, shows LAMP expression high in the perirhinal region of the cortex (pr) and sparse in the dorsal, non-limbic cortex. LAMP expression in the embryo is high in the hippocampus (h) and midthalamic region, including the mediodorsal nucleus of the thalamus (md). In sections from adult rat brain, hybridization was high in the perirhinal cortex (pr), amygdala (a), hypothalamus and medial thalamic region (md), but sparse in the sensorimotor cortex. When a riboprobe spanning regions of the LAMP cDNA with high homology with OBCAM and neurotrimin was used, additional staining was observed.

These LAMP staining patterns are closely analogous to, though not identical with, the patterns observed with the 2G9 antibody. Chesselet et al., *Neurosci.* 40: 725–733, 1991; Levitt, *Science* 223: 299–301, 1984.

EXAMPLE 5

Recombinant Expression of LAMP in Chinese Hamster Ovary Cells

The rat cDNA was subcloned into the EcoRI site of the eukaryotic expression vector pcDNA3 (Invitrogen, San Diego, Calif.). CHO cells were transfected with 10–15 µg of this subcloned vector or, to create control cells, with the pcDNA3 vector lacking an insert. Transfection was accomplished using the calcium phosphate co-precipitation method. Ishiura et al., *Mol. Cell Biol.* 2, 607–616, 1982: 5463–5467, 1977. Stably transformed cells were selected by growth in the presence of G418 (Life Technologies, Grand Island, N.J.) and subcloned by limiting dilution (to select a genetically homogeneous colony). The LAMP cDNA transfected cells were designated $CHO_L$, while the control transformants were designated $CHO_{Vector}$.

To confirm the cell-surface expression of LAMP, the $CHO_L$ cells were incubated with mouse anti-LAMP, washed four times with DMEM/10% FCS, incubated with FITC conjugated donkey anti-mouse antibody (Jackson, Immunoresearch, West Grove, Pa.), fixed with 4% formaldehyde, and mounted in glycerol/PBS with 5% propyl gallate.

To test whether $CHO_L$ cells can bind external LAMP, fluorescent synthetic beads of 2 μm diameter, which have reactive sites for covalently linking protein (Covasphere™ beads, Duke Scientific, Palo Alto, Calif.), were coated with native LAMP that had been released from hippocampal membranes with PI-specific phospholipase C. The beads were incubated with the recombinant cells and the extent of binding to the cell surface determined.

The $CHO_L$ cells were found to have cell-surface LAMP immunoreactivity, while the $CHO_{Vector}$ cells did not. When the $CHO_L$ cells were treated with PI-specific phospholipase C and the released proteins were analyzed by Western blot, a LAMP immunoreactive band of 55 kDa was identified. The released protein from hippocampal membranes has an apparent molecular weight of 64–68 kDa, probably reflecting a greater degree of glycosylation. The LAMP-coated Covasphere™ beads were found to bind the $CHO_L$ cells.

EXAMPLE 6

Differentiation Promotion by the $CHO_L$ Cells

The growth of various embryonic cell populations on substrata of $CHO_L$ or $CHO_{Vector}$ was tested. The first two cell populations were LAMP-expressing cells from (A) the hippocampus and (B) the perirhinal cortex. Non-LAMP-expressing cells from (C) the olfactory bulb and (D) the visual cortex were also tested. Primary neurons from E16 embryos were prepared as outlined by Ferri and Levitt, Cerebral Cortex 3; 187–198, 1993. In some experiments, the cells were marked by adding lipophilic dye PKH26 (Sigma Chemical Co., St. Louis, Mo.); if they were not so marked, an antibody stain was used later in the experiment to identify neural cells. The cells were plated in DMEM/10% FCS at a density of $5 \times 10^3$ cells/ml, 1 ml per $cm^2$, onto coverslips on which there were monolayers of transformed CHO cells. After 48 hours in culture, the cells attached to the coverslips were fixed with 4% formaldehyde and, if the neural cells were not dye-marked, stained for neural cells with anti-MAP2, as described in Ferri and Levitt, Cerebral Cortex 3: 187–198, 1993. For each category in the experiment, six coverslips were examined and the longest neuron in a randomly selected field of 10–15 process-bearing cells was measured.

When grown on the $CHO_L$ cells, the LAMP-expressing cells exhibited extensive neurite growth within 24 hours, with well-differentiated morphologies, often including long neurites. These cells grew poorly on $CHO_{Vector}$ cells (see FIG. 5). When the neural cells were pre-treated with LAMP antibody, the length of the neurites extended by the $CHO_L$ cells was significantly reduced (FIG. 5). The olfactory and visual cells bound the $CHO_L$ substratum, but differentiated poorly, extending shorter neurites. Additionally, these olfactory and visual cells grew equivalently on $CHO_{Vector}$ and $CHO_L$ cells.

EXAMPLE 7

Interference in Post Natal Development of an Intrahippocampal Circuit by Antibodies to LAMP Newborn Sprague-Dawley rats were injected intraventricularly with Fab fragments of anti-LAMP (n=15), control anti-paramyosin IgG (n=14), and anti-L1 (n=5). Anti-L1, which binds to developing axons, was as described by Sweadner, J. Neurosci. 3: 2504–2517, 1983. All antisera was purified on a protein A column using a protein A affinity enhancement buffer (the MAPSII buffer system used as recommended by the supplier, Biorad Labs, Hercules, Calif.). Fab fragments were prepared from the antisera by digestion with immobilized papain (Pierce, Rockford, Ill.) and purified by protein-A affinity chromatography. The Fab fragments (10 μg in 10 μl of saline) were injected on postnatal day 0, 2, 4 and 6 into the cisterna magna using a 32-gauge needle. On day 9, the animals were sacrificed by transcardial perfusion with 4.9% sodium sulfide in 0.1 M phosphate buffer (pH 7.4). Brains were fixed in Carnoy's solution together with 1.2% sodium sulfide. Paraffin sections of the brains were prepared for mossy fiber staining using the Timm method. Haug, Adv. Anat Embryol. Cell Biol. 47: 1–71, 1973. Subfields were analyzed for density of innervation using the Bioquant OS/2 image analysis system (R & M Biometrics, Nashville, Tenn.).

The excitatory glutaminergic mossy fiber projection of granule cells to pyramidal neurons of the hippocampus express LAMP during development. Zacco et al., J. Neurosci. 10: 73–90, 1990; Keller and Levitt, Neuroscience 28 455–474, 1989. The anti-LAMP treatment, but not the other antibody treatments, resulted in an uncharacteristically diffuse pattern for this mossy fiber projection. Detailed examination found many misdirected fibers. Quantitatively, the treatment resulted in a six fold increase in the area occupied by mossy fiber projections.

EXAMPLE 8

Isolation of the 5' Untranscribed Region of the LAMP Gene

Plaques from a genomic library derived from the 129/Rej mouse strain and cloned into Lambda Fix II (Stratagene, LaJolla, Calif.) were screened with a $^{32}$P-labelled probe generated by randomly priming a plasmid containing nucleotides 1–453 of SEQ ID NO:2. Two positive clones were isolated and sequenced to generate the sequence information of FIG. 5 (SEQ ID NOs: 19 and 20).

EXAMPLE 9

Cell-type Specific Expression of CAT Vectors

The nucleotide sequence (nt 1–864) of the mouse genomic SEQ ID NO: 19 was amplified by PCR using the following primers: Primer 1: CCGAAGCTTCTGCAGTAT-GCCTTCCTATCCATGTGTATG (SEQ ID NO:28) Primer 2: ATATCTAGATAGTGGTACCGAGTTGTTC-CGCGGTGGACTGCGTGTGCGC (SEQ ID NO:29) and subcloned into the promoterless pCTA-Basic Vector (Promega, Madison, Wis.) which contains the CAT (Chloramphenicol acetyltransferase) reporter gene. Cell lines were transiently transfected with the pCAT-864 construct, and as a control, with a vector containing an active promoter and the cat gene (Promega, Madison, Wis.) using the calcium phosphate or the DEAE-Dextran method (Ausubel et al., Current Protocols in Molecular Biology, Wiley Press, 1993).

Promoter activity on induction of the cat gene was measured by the CAT activity assay using 14C-Chloramphenicol and acetyl CoA as substrates for CAT, and separating the acetylated 14C-chloramphenicol products by thin layer chromatography. The product was detected by autoradiography (Ausubel et al., Current Protocols in Molecular

*Biology*, Wiley Press, 1993) and quantitated by liquid scintillation counting.

This fragment of the genomic DNA induces expression of the cat gene in SN56 cells (a limbic neuronal cell line described in H. J. Lee et al., *Dev. Brain Res.* 52, 219–228, 1990), but not in N2A cells (a neuroblastoma cell line) or CHO cells (a non-neuronal cell line).

EXAMPLE 10

Construction of Deletion Mutants

To examine the structure-function relationships of the various domains of LAMP, a number of deletion mutants have been constructed. Nucleotides 17 through 1000 of SEQ ID NO:2 (which encodes amino acids 1–315) was generated by PCR amplification. The primers had overhang regions that were designed to create terminal restriction sites which were used to insert the amplified sequence into the pcDNA3 expression vector. The 3' primer overhang also included sequence for encoding six repeats of histidine followed by a stop codon. CHO cells were transformed with the recombinant expression vector and cultured. The recombinant protein produced by these cells was exported into the culture medium. To purify the protein, the medium was passed over an ionic nickel column (Ni-NTA, available from Qiagene, Chatsworth, Calif.), which bound the poly-His tail of the recombinant protein.

An analogous strategy was used to create recombinant proteins for nucleotides 374 through 1001 (amino acids 107–315, including the second and third immunoglobulin-like region) and nucleotides 713 through 907 (amino acids 220–284, including substantially all of the third immunoglobulin-like domain). These peptide sequences were expressed as fusion proteins together with a maltose binding domain. To do this, the sequences were subcloned into the pMaltose vector available from New England Biolabs (Beverly, Mass.) and the recombinant vectors were used to transform bacteria. The fusion proteins were isolated from bacterial lysates by column chromatography on an amylose affinity resin (available from New England Biolabs).

These proteins are tested by, for instance, the methods outlined above to determine whether they had LAMP binding activity and/or the ability to promote the formation of neurites.

---

What is claimed is:

1. An isolated polypeptide comprising residues 29 to 315 of SEQ ID NO:8, or a sequence differing therefrom by no more than two of the following variations: $Leu^{55}$ changes to $Val^{55}$, $Ser^{91}$ changes to $Ala^{91}$, or $Thr^{171}$ changes to $Leu^{171}$.

2. The isolated polypeptide of claim 1, wherein the isolated polypeptide comprises a heterologous amino acid sequence fused to the comprised amino acid sequence.

3. The isolated polypeptide of claim 1, wherein the comprised amino acid sequence differs from the 29 to 315 SEQ ID NO:8 sequence by no more than one of the following variations: $Leu^{55}$ changes to $Val^{55}$, $Ser^{91}$ changes to $Ala^{91}$, or $Thr^{171}$ changes to $Leu^{171}$.

4. The isolated polypeptide of claim 3, wherein the isolated polypeptide comprises a heterologous amino acid sequence fused to the comprised amino acid sequence.

5. The isolated polypeptide of claim 1, wherein the comprised amino acid sequence matches the 29 to 315 SEQ ID NO:8 sequence.

6. The isolated polypeptide of claim 5, wherein the isolated polypeptide comprises a heterologous amino acid sequence fused to the comprised amino acid sequence.

7. An isolated polypeptide comprising residues 1 to 315 of SEQ ID NO:8, or a sequence differing therefrom by (a) no more than two of the following variations: $Leu^{55}$ changes to $Val^{55}$, $Ser^{91}$ changes to $Ala^{91}$, or $Thr^{171}$ changes to $Leu^{171}$ and (b) no more than the following additional variations: $Leu^{20}$ changes to $Ser^{20}$ or $Cys^{21}$ changes to $His^{21}$.

8. The isolated polypeptide of claim 7, wherein the isolated polypeptide comprises a heterologous amino acid sequence fused to the comprised amino acid sequence.

9. An isolated polypeptide comprising residues 1 to 315 of SEQ ID NO:8.

10. The isolated polypeptide of claim 9, wherein the isolated polypeptide comprises a heterologous amino acid sequence fused to the comprised amino acid sequence.

11. An isolated polypeptide comprising residues 29 to 338 of SEQ ID NO:8, or a sequence differing therefrom by (a) no more than two of the following variations: $Leu^{55}$ changes to $Val^{55}$, $Ser^{91}$ changes to $Ala^{91}$, $Thr^{171}$ changes to $Leu^{171}$, or $Leu^{332}$ changes to $Phe^{332}$.

12. The isolated polypeptide of claim 11, wherein the isolated polypeptide comprises a heterologous amino acid sequence fused to the comprised amino acid sequence.

13. The isolated polypeptide of claim 11, wherein the comprised amino acid sequence matches the 29 to 338 SEQ ID NO:8 sequence.

14. The isolated polypeptide of claim 13, wherein the isolated polypeptide comprises a heterologous amino acid sequence fused to the comprised amino acid sequence.

15. An isolated polypeptide comprising residues 1 to 338 of SEQ ID NO:8, or a sequence differing therefrom by (a) no more than two of the following variations: $Leu^{55}$ changes to $Val^{55}$, $Ser^{91}$ changes to $Ala^{91}$, $Thr^{171}$ changes to $Leu^{171}$, or $Leu^{332}$ changes to $Phe^{332}$, and (b) no more than the following additional variations: $Leu^{20}$ changes to $Ser^{20}$ or $Cys^{21}$ changes to $His^{21}$.

16. The isolated polypeptide of claim 15, wherein the isolated polypeptide comprises a heterologous amino acid sequence fused to the comprised amino acid sequence.

17. An isolated polypeptide comprising residues 1 to 338 of SEQ ID NO:8.

18. The isolated polypeptide of claim 17, wherein the isolated polypeptide comprises a heterologous amino acid sequence fused to the comprised amino acid sequence.

* * * * *

SEQUENCE LISTING (1) GENERAL INFORMATION:

(iii) NUMBER OF SEQUENCES: 29

(2) INFORMATION FOR SEQ ID NO:1:

(i) SEQUENCE CHARACTERISTICS:
      (A) LENGTH: 977 base pairs
      (B) TYPE: nucleic acid
      (C) STRANDEDNESS: double
      (D) TOPOLOGY: linear (ix) FEATURE:
      (A) NAME/KEY: Coding Sequence
      (B) LOCATION: 2...976
      (D) OTHER INFORMATION:

(xi) SEQUENCE DESCRIPTION: SEQ ID NO:1:

```
G GAT CGG AAA CAG TTG CCA CTG GTC CTA CTG AGA TTG CTC TGC CTT CTT      49
  Asp Arg Lys Gln Leu Pro Leu Val Leu Leu Arg Leu Leu Cys Leu Leu
   1               5                  10                  15

CCC ACA GGA CTG CCT GTT CGC AGC GTG GAT TTT AAC CGA GGC ACG GAC        97
Pro Thr Gly Leu Pro Val Arg Ser Val Asp Phe Asn Arg Gly Thr Asp
             20                  25                  30

AAC ATC ACC GTG AGG CAG GGG GAC ACA GCC ATC CTC AGG TGC GTT CTA       145
Asn Ile Thr Val Arg Gln Gly Asp Thr Ala Ile Leu Arg Cys Val Leu
         35                  40                  45

GAA GAC AAG AAC TCA AAG GTG GCC TGG TTG AAC CGT TCT GGC ATC ATT       193
Glu Asp Lys Asn Ser Lys Val Ala Trp Leu Asn Arg Ser Gly Ile Ile
     50                  55                  60

TTT GCT GGA CAT GAC AAG TGG TCT CTG GAC CCA CGG GTT GAG CTG GAG       241
Phe Ala Gly His Asp Lys Trp Ser Leu Asp Pro Arg Val Glu Leu Glu
 65                  70                  75                  80

AAA CGC CAT TCT CTG GAA TAC AGC CTC CGA ATC CAG AAG GTG GAT GTC       289
Lys Arg His Ser Leu Glu Tyr Ser Leu Arg Ile Gln Lys Val Asp Val
                 85                  90                  95

TAT GAT GAG GGT TCC TAC ACT TGC TCA GTT CAG ACA CAG CAT GAG CCC       337
```

```
                Tyr Asp Glu Gly Ser Tyr Thr Cys Ser Val Gln Thr Gln His Glu Pro
                            100                 105                 110

AAG ACC TCC CAA GTT TAC TTG ATC GTA CAA GTC CCA CCA AAG ATC TCC         385
Lys Thr Ser Gln Val Tyr Leu Ile Val Gln Val Pro Pro Lys Ile Ser
            115                 120                 125

AAT ATC TCC TCG GAT GTC ACT GTG AAT GAG GGC AGC AAC GTG ACT CTG         433
Asn Ile Ser Ser Asp Val Thr Val Asn Glu Gly Ser Asn Val Thr Leu
130                 135                 140

GTC TGC ATG GCC AAT GGC CGT CCT GAA CCT GTT ATC ACC TGG AGA CAC         481
Val Cys Met Ala Asn Gly Arg Pro Glu Pro Val Ile Thr Trp Arg His
145                 150                 155                 160

CTT ACA CCA ACT GGA AGG GAA TTT GAA GGA GAA GAA GAA TAT CTG GAG         529
Leu Thr Pro Thr Gly Arg Glu Phe Glu Gly Glu Glu Glu Tyr Leu Glu
                165                 170                 175

ATC CTT GGC ATC ACC AGG GAG CAG TCA GGC AAA TAT GAG TGC AAA GCT         577
Ile Leu Gly Ile Thr Arg Glu Gln Ser Gly Lys Tyr Glu Cys Lys Ala
            180                 185                 190

GCC AAC GAG GTC TCC TCG GCG GAT GTC AAA CAA GTC AAG GTC ACT GTG         625
Ala Asn Glu Val Ser Ser Ala Asp Val Lys Gln Val Lys Val Thr Val
                195                 200                 205

AAC TAT CCT CCC ACT ATC ACA GAA TCC AAG AGC AAT GAA GCC ACC ACA         673
Asn Tyr Pro Pro Thr Ile Thr Glu Ser Lys Ser Asn Glu Ala Thr Thr
            210                 215                 220

GGA CGA CAA GCT TCA CTC AAA TGT GAG GCC TCG GCA GTG CCT GCA CCT         721
Gly Arg Gln Ala Ser Leu Lys Cys Glu Ala Ser Ala Val Pro Ala Pro
225                 230                 235                 240

GAC TTT GAG TGG TAC CGG GAT GAC ACT AGG ATA AAT AGT GCC AAT GGC         769
Asp Phe Glu Trp Tyr Arg Asp Asp Thr Arg Ile Asn Ser Ala Asn Gly
                245                 250                 255

CTT GAG ATT AAG AGC ACG GAG GGC CAG TCT TCC CTG ACG GTG ACC AAC         817
Leu Glu Ile Lys Ser Thr Glu Gly Gln Ser Ser Leu Thr Val Thr Asn
            260                 265                 270

GTC ACT GAG GAG CAC TAC GGC AAC TAC ACC TGT GTG GCT GCC AAC AAG         865
Val Thr Glu Glu His Tyr Gly Asn Tyr Thr Cys Val Ala Ala Asn Lys
            275                 280                 285

CTG GGG GTC ACC AAT GCC AGC CTA GTC CTT TTC AGA CCT GGG TCG GTG         913
Leu Gly Val Thr Asn Ala Ser Leu Val Leu Phe Arg Pro Gly Ser Val
            290                 295                 300

AGA GGA ATA AAT GGA TCC ATC AGT CTG GCC GTA CCA CTG TGG CTG CTG         961
Arg Gly Ile Asn Gly Ser Ile Ser Leu Ala Val Pro Leu Trp Leu Leu
305                 310                 315                 320

GCA GCA TCT CTG CTC T                                                   977
Ala Ala Ser Leu Leu
                325

(2) INFORMATION FOR SEQ ID NO:2:

(i) SEQUENCE CHARACTERISTICS:
        (A) LENGTH: 325 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:2:

Asp Arg Lys Gln Leu Pro Leu Val Leu Leu Arg Leu Leu Cys Leu Leu
1               5                   10                  15

Pro Thr Gly Leu Pro Val Arg Ser Val Asp Phe Asn Arg Gly Thr Asp
                20                  25                  30
```

```
Asn Ile Thr Val Arg Gln Gly Asp Thr Ala Ile Leu Arg Cys Val Leu
         35                  40                  45

Glu Asp Lys Asn Ser Lys Val Ala Trp Leu Asn Arg Ser Gly Ile Ile
 50                  55                  60

Phe Ala Gly His Asp Lys Trp Ser Leu Asp Pro Arg Val Glu Leu Glu
 65                  70                  75                  80

Lys Arg His Ser Leu Glu Tyr Ser Leu Arg Ile Gln Lys Val Asp Val
                 85                  90                  95

Tyr Asp Glu Gly Ser Tyr Thr Cys Ser Val Gln Thr Gln His Glu Pro
                100                 105                 110

Lys Thr Ser Gln Val Tyr Leu Ile Val Gln Val Pro Pro Lys Ile Ser
        115                 120                 125

Asn Ile Ser Ser Asp Val Thr Val Asn Glu Gly Ser Asn Val Thr Leu
        130                 135                 140

Val Cys Met Ala Asn Gly Arg Pro Glu Pro Val Ile Thr Trp Arg His
145                 150                 155                 160

Leu Thr Pro Thr Gly Arg Glu Phe Glu Gly Glu Glu Tyr Leu Glu
                165                 170                 175

Ile Leu Gly Ile Thr Arg Glu Gln Ser Gly Lys Tyr Glu Cys Lys Ala
                180                 185                 190

Ala Asn Glu Val Ser Ser Ala Asp Val Lys Gln Val Lys Val Thr Val
            195                 200                 205

Asn Tyr Pro Pro Thr Ile Thr Glu Ser Lys Ser Asn Glu Ala Thr Thr
        210                 215                 220

Gly Arg Gln Ala Ser Leu Lys Cys Glu Ala Ser Ala Val Pro Ala Pro
225                 230                 235                 240

Asp Phe Glu Trp Tyr Arg Asp Asp Thr Arg Ile Asn Ser Ala Asn Gly
                245                 250                 255

Leu Glu Ile Lys Ser Thr Glu Gly Gln Ser Ser Leu Thr Val Thr Asn
                260                 265                 270

Val Thr Glu Glu His Tyr Gly Asn Tyr Thr Cys Val Ala Ala Asn Lys
        275                 280                 285

Leu Gly Val Thr Asn Ala Ser Leu Val Leu Phe Arg Pro Gly Ser Val
        290                 295                 300

Arg Gly Ile Asn Gly Ser Ile Ser Leu Ala Val Pro Leu Trp Leu Leu
305                 310                 315                 320

Ala Ala Ser Leu Leu
                325

(2) INFORMATION FOR SEQ ID NO:3:

(i) SEQUENCE CHARACTERISTICS:
        (A) LENGTH: 1238 base pairs
        (B) TYPE: nucleic acid
        (C) STRANDEDNESS: double
        (D) TOPOLOGY: linear (ix) FEATURE:
        (A) NAME/KEY: Coding Sequence
        (B) LOCATION: 56...1069
        (D) OTHER INFORMATION:

(xi) SEQUENCE DESCRIPTION: SEQ ID NO:3:

GTGGCCAGCA GCGCGCACAC GCGAGTCCAC CGCTGACCAA CTCGCCGAGG CCACC ATG      58
                                                              Met
                                                                1

GTC GGG AGA GTT CAA CCT GAT CGG AAA CAG TTG CCA CTG GTC CTA CTG     106
```

```
Val Gly Arg Val Gln Pro Asp Arg Lys Gln Leu Pro Leu Val Leu Leu
            5                  10                 15

AGA CTG CTC TGC CTT CTT CCC ACA GGA CTG CCC GTT CGC AGC GTG GAT       154
Arg Leu Leu Cys Leu Leu Pro Thr Gly Leu Pro Val Arg Ser Val Asp
        20                  25                  30

TTT AAC CGA GGC ACG GAC AAC ATC ACC GTG AGG CAG GGG GAC ACG GCC       202
Phe Asn Arg Gly Thr Asp Asn Ile Thr Val Arg Gln Gly Asp Thr Ala
 35                  40                  45

ATC CTC AGG TGT GTG GTA GAA GAC AAG AAC TCG AAA GTG GCC TGG TTG       250
Ile Leu Arg Cys Val Val Glu Asp Lys Asn Ser Lys Val Ala Trp Leu
50                  55                  60                  65

AAC CGC TCT GGC ATC ATC TTC GCT GGA CAC GAC AAG TGG TCT CTG GAC       298
Asn Arg Ser Gly Ile Ile Phe Ala Gly His Asp Lys Trp Ser Leu Asp
                70                  75                  80

CCT CGG GTT GAG CTG GAG AAA CGC CAT GCT CTG GAA TAC AGC CTC CGA       346
Pro Arg Val Glu Leu Glu Lys Arg His Ala Leu Glu Tyr Ser Leu Arg
            85                  90                  95

ATC CAG AAG GTG GAT GTC TAT GAT GAA GGA TCC TAC ACA TGC TCA GTT       394
Ile Gln Lys Val Asp Val Tyr Asp Glu Gly Ser Tyr Thr Cys Ser Val
        100                 105                 110

CAG ACA CAG CAT GAG CCC AAG ACC TCT CAA GTT TAC TTG ATT GTA CAA       442
Gln Thr Gln His Glu Pro Lys Thr Ser Gln Val Tyr Leu Ile Val Gln
    115                 120                 125

GTT CCA CCA AAG ATC TCC AAC ATC TCC TCG GAT GTC ACT GTG AAT GAG       490
Val Pro Pro Lys Ile Ser Asn Ile Ser Ser Asp Val Thr Val Asn Glu
130                 135                 140                 145

GGC AGC AAT GTA ACC CTG GTC TGC ATG GCC AAT GGG CGC CCT GAA CCT       538
Gly Ser Asn Val Thr Leu Val Cys Met Ala Asn Gly Arg Pro Glu Pro
                150                 155                 160

GTT ATC ACC TGG AGA CAC CTT ACA CCA CTT GGA AGA GAA TTT GAA GGA       586
Val Ile Thr Trp Arg His Leu Thr Pro Leu Gly Arg Glu Phe Glu Gly
            165                 170                 175

GAA GAA GAA TAT CTG GAG ATC CTA GGC ATC ACC AGG GAA CAG TCA GGC       634
Glu Glu Glu Tyr Leu Glu Ile Leu Gly Ile Thr Arg Glu Gln Ser Gly
        180                 185                 190

AAA TAT GAG TGC AAG GCT GCC AAC GAG GTC TCC TCC GCG GAT GTC AAA       682
Lys Tyr Glu Cys Lys Ala Ala Asn Glu Val Ser Ser Ala Asp Val Lys
    195                 200                 205

CAA GTC AAG GTC ACT GTG AAC TAT CCA CCC ACC ATC ACA GAG TCT AAG       730
Gln Val Lys Val Thr Val Asn Tyr Pro Pro Thr Ile Thr Glu Ser Lys
210                 215                 220                 225

AGC AAT GAA GCC ACC ACA GGA CGA CAA GCT TCC CTC AAA TGT GAA GCC       778
Ser Asn Glu Ala Thr Thr Gly Arg Gln Ala Ser Leu Lys Cys Glu Ala
                230                 235                 240

TCA GCG GTG CCT GCA CCT GAC TTT GAG TGG TAC CGG GAT GAC ACC AGG       826
Ser Ala Val Pro Ala Pro Asp Phe Glu Trp Tyr Arg Asp Asp Thr Arg
            245                 250                 255

ATA AAC AGT GCA AAC GGC CTT GAG ATT AAG AGC ACT GAG GGC CAG TCC       874
Ile Asn Ser Ala Asn Gly Leu Glu Ile Lys Ser Thr Glu Gly Gln Ser
        260                 265                 270

TCC CTG ACG GTG ACC AAC GTC ACT GAG GAA CAC TAC GGC AAC TAT ACC       922
Ser Leu Thr Val Thr Asn Val Thr Glu Glu His Tyr Gly Asn Tyr Thr
    275                 280                 285

TGT GTG GCT GCC AAC AAG CTC GGC GTC ACC AAT GCC AGC CTA GTC CTT       970
Cys Val Ala Ala Asn Lys Leu Gly Val Thr Asn Ala Ser Leu Val Leu
290                 295                 300                 305

TTC AGA CCC GGG TCG GTG AGA GGA ATC AAC GGA TCC ATC AGT CTG GCC      1018
Phe Arg Pro Gly Ser Val Arg Gly Ile Asn Gly Ser Ile Ser Leu Ala
                310                 315                 320
```

```
GTA CCA CTG TGG CTG CTG GCA GCG TCC CTG TTC TGC CTT CTC AGC AAA    1066
Val Pro Leu Trp Leu Leu Ala Ala Ser Leu Phe Cys Leu Leu Ser Lys
        325                 330                 335

TGT TAATAGAATA AAAATTTAAA AATAATTACA AAACACACAA AAATGCGTCA CACAGA  1125
Cys

TACAGAGAGA GAGAGAGAGA GAGAGAGAAA GTACAAGATG GGGGGAGACT ATTGTTTCAC  1185

AAGATTGTGT GTTTATAAAT GAAGGGGGGA TATGAAAAAA ATGAAGAAAA TAC         1238
```

(2) INFORMATION FOR SEQ ID NO:4:

(i) SEQUENCE CHARACTERISTICS:
        (A) LENGTH: 338 amino acids
        (B) TYPE: amino acid
        (C) STRANDEDNESS: single
        (D) TOPOLOGY: linear (xi) SEQUENCE DESCRIPTION: SEQ ID NO:4:

```
Met Val Gly Arg Val Gln Pro Asp Arg Lys Gln Leu Pro Leu Val Leu
 1               5                  10                  15

Leu Arg Leu Leu Cys Leu Leu Pro Thr Gly Leu Pro Val Arg Ser Val
            20                  25                  30

Asp Phe Asn Arg Gly Thr Asp Asn Ile Thr Val Arg Gln Gly Asp Thr
        35                  40                  45

Ala Ile Leu Arg Cys Val Val Glu Asp Lys Asn Ser Lys Val Ala Trp
    50                  55                  60

Leu Asn Arg Ser Gly Ile Ile Phe Ala Gly His Asp Lys Trp Ser Leu
65                  70                  75                  80

Asp Pro Arg Val Glu Leu Glu Lys Arg His Ala Leu Glu Tyr Ser Leu
                85                  90                  95

Arg Ile Gln Lys Val Asp Val Tyr Asp Glu Gly Ser Tyr Thr Cys Ser
            100                 105                 110

Val Gln Thr Gln His Glu Pro Lys Thr Ser Gln Val Tyr Leu Ile Val
        115                 120                 125

Gln Val Pro Pro Lys Ile Ser Asn Ile Ser Ser Asp Val Thr Val Asn
    130                 135                 140

Glu Gly Ser Asn Val Thr Leu Val Cys Met Ala Asn Gly Arg Pro Glu
145                 150                 155                 160

Pro Val Ile Thr Trp Arg His Leu Thr Pro Leu Gly Arg Glu Phe Glu
                165                 170                 175

Gly Glu Glu Glu Tyr Leu Glu Ile Leu Gly Ile Thr Arg Glu Gln Ser
            180                 185                 190

Gly Lys Tyr Glu Cys Lys Ala Ala Asn Glu Val Ser Ser Ala Asp Val
        195                 200                 205

Lys Gln Val Lys Val Thr Val Asn Tyr Pro Pro Thr Ile Thr Glu Ser
    210                 215                 220

Lys Ser Asn Glu Ala Thr Thr Gly Arg Gln Ala Ser Leu Lys Cys Glu
225                 230                 235                 240

Ala Ser Ala Val Pro Ala Pro Asp Phe Glu Trp Tyr Arg Asp Asp Thr
                245                 250                 255

Arg Ile Asn Ser Ala Asn Gly Leu Glu Ile Lys Ser Thr Glu Gly Gln
            260                 265                 270

Ser Ser Leu Thr Val Thr Asn Val Thr Glu Glu His Tyr Gly Asn Tyr
        275                 280                 285

Thr Cys Val Ala Ala Asn Lys Leu Gly Val Thr Asn Ala Ser Leu Val
    290                 295                 300
```

```
Leu Phe Arg Pro Gly Ser Val Arg Gly Ile Asn Gly Ser Ile Ser Leu
305                 310                 315                 320

Ala Val Pro Leu Trp Leu Leu Ala Ala Ser Leu Phe Cys Leu Leu Ser
                325                 330                 335

Lys Cys (2) INFORMATION FOR SEQ ID NO:5:

(i) SEQUENCE CHARACTERISTICS:
        (A) LENGTH: 1851 base pairs
        (B) TYPE: nucleic acid
        (C) STRANDEDNESS: double
        (D) TOPOLOGY: linear (ix) FEATURE:
        (A) NAME/KEY: Coding Sequence
        (B) LOCATION: 877...1032
        (D) OTHER INFORMATION:

(xi) SEQUENCE DESCRIPTION: SEQ ID NO:5:

CTGCAGTATG CCTTCCTATC CATGTGTATG TAACTCCATT TGTCAAGGTT TGCATTTCTT    60

TCTTGCCATG CCTTCCCTCT CCTTTCCTGG ACCCTTTCTC CTGTCCTTTT ACAGCTTAAG   120

TCCACCTCCC CTTCCCTGTC TTAACAGTAC CTCTGAGCCC CATCCCCTCT TCTTAAGGAA   180

ATCAGCCAGG CCTCAGATGG AGCTGTTGTC CTGACAACCC AAAGGCGCAT CAGGCTTTCA   240

TTGAGGCTGG CTGCTGGTGA AGAGGGCAGT TGTGCAAAGC AAGGGGCCAC GCTGAGGGGT   300

GGGAGGAGGG GATGACGTGG TGGGGCTGTT GAAAACCAGC AGGGTAGGGG GGAGGTGCTG   360

AGTAGAGAGA GAACAGGGAC TGGAGGGAGA AACAAGAAAG AGGAGGGGGA GAGAGCTCCT   420

GGGTTGCTGC CGCTACTGCT GCTGCTGCTG CAAGAGGCTG TTTCTTTACT CTCCCTGGCA   480

GGCTCTCCTG CTGCCTGGGA AAGTGGGTTA CAGAGGGAAG CAGCTCAGCC CAGACGCTGG   540

CAGAGAAGCA GCCAGCTACA GAGAGTCTAA GGAAGCACCC CTGCCATTGA CAGTCGCCTC   600

CTCATCATTA AAGCATTTTA TATTTGCACT CTTCCTTCGG AAAATTTGTT CCTCCACTTT   660

CTCCCCGACT CCTGCTTGGA TTTGATGAGG GCTTTGTTAA ATCCCAGAGG AAAAGAGACT   720

AAGCGAGGGA AAGAGCAAGG CAAAGTGGAA GGGAGTGCGC GCTGGACCCG CCCGAGCAGC   780

CTTGGCAGTG GCTGCGAGCC CCGCGCGCTA GAGCCCCTCT CCGTGTCCAG CAGCGCGCAC   840

ACGCAGTCCA CCGCGGACCA ACTCGCCGAG GCCACC ATG GTC GGG AGA GTT CAG   894
                                        Met Val Gly Arg Val Gln
                                         1               5

CCC GAT CGG AAA CAG TTG CCG CTG GTC CTA CTG AGA TCT TCC CAC CTT    942
Pro Asp Arg Lys Gln Leu Pro Leu Val Leu Leu Arg Ser Ser His Leu
            10                  15                  20

CTT CCC ACA GGA CTG CCC GTT CGC AGC GTG GAT TTT AAC CGA GGC ACG    990
Leu Pro Thr Gly Leu Pro Val Arg Ser Val Asp Phe Asn Arg Gly Thr
        25                  30                  35

GAC AAC ATC ACC GTG AGA CAG GGG GAC ACG GCC ATC CTC AGG TAGGGCTTG 1041
Asp Asn Ile Thr Val Arg Gln Gly Asp Thr Ala Ile Leu Arg
    40                  45                  50

CGAGCAACTT TTCTGGTGTG TGTGTGTGTG TGTGTGTGTG TGTGTGTGTG TGTGTGTGTG  1101

TGTAATAGTG AACTCCAGCT GCCCTGGGTT AGTGGGCGTG TGTGTGTGTG TGTGTGTGTG  1161

TGTGTGTCCC TTACGTTACT CGACTTGAAG ATTTAGCCAG GAACAAAATT TAAGGCGAGT  1221

CTGGTCCCTG TCAAGAGCCA AGGGTGCTTT TGGAATGTTG TTCCGTTCTT TGAATGTTGT  1281

TTTCTCTAGT CAAGAAAGCC GAACTTTATC TATGGCATTA GTGGCATTGG GCTGTATCAT  1341

GCTGTGGTAA TTGCTCACGC TTGGCACTTA GACTTTTGTT GAGATTCTTC TATTCAGACA  1401
```

-continued

```
CAAGAGTTGT TGAGTTATGG CTTTCAAAAC GTGGTACGCA AGGCTGCATT CTCTTGTTCG    1461

TGTGTGTGTG TGTGTGTGTG TGTGTGTGTG TGTGTGTGTG TGTTGCTCAG CAAGGCTCAG    1521

TCTGCCCTAG CAGTAGTTCC TGATAGAAGA CTTTCTGTAA AGATCTCTGA ATTGACATCA    1581

TAGGCAATAA ATCAATCTTA CAACTTTGGC ATGATTACTG AGGCTTTTTG GGAATGTGGA    1641

CAGAAATCAA CACGAGAATG AGAGAACGGA AGGAAAGGAT CCAGCCTAAT GGCAGGCCGT    1701

TAAGAATAGA AAACTTAAAC AGAGGAGGAG AAGGCATTAA CCTGATATTA CATTAGATAC    1761

TACAAATTGA TCATTGAGTT CAAAGTCTTA TGCTTATGCA GCTCTGCCAA CGTCCGCAAT    1821

ATAATTTGGG ATGGAAATTT GGAAAAGCTT                                    1851
```

(2) INFORMATION FOR SEQ ID NO:6:

(i) SEQUENCE CHARACTERISTICS:
        (A) LENGTH: 52 amino acids
        (B) TYPE: amino acid
        (C) STRANDEDNESS: single
        (D) TOPOLOGY: linear (xi) SEQUENCE DESCRIPTION: SEQ ID NO:6:

```
Met Val Gly Arg Val Gln Pro Asp Arg Lys Gln Leu Pro Leu Val Leu
 1               5                  10                  15

Leu Arg Leu Ser His Leu Leu Pro Thr Gly Leu Pro Val Arg Ser Val
             20                  25                  30

Asp Phe Asn Arg Gly Thr Asp Asn Ile Thr Val Arg Gln Gly Asp Thr
         35                  40                  45

Ala Ile Leu Arg
     50
```

(2) INFORMATION FOR SEQ ID NO:7:

(i) SEQUENCE CHARACTERISTICS:
        (A) LENGTH: 1014 base pairs
        (B) TYPE: nucleic acid
        (C) STRANDEDNESS: double
        (D) TOPOLOGY: linear (ix) FEATURE:
        (A) NAME/KEY: Coding Sequence
        (B) LOCATION: 1...1014
        (D) OTHER INFORMATION:

(xi) SEQUENCE DESCRIPTION: SEQ ID NO:7:

```
ATG GTC GGG AGA GTT CAA CCT GAT CGG AAA CAG TTG CCA CTG GTC CTA      48
Met Val Gly Arg Val Gln Pro Asp Arg Lys Gln Leu Pro Leu Val Leu
 1               5                  10                  15

CTG AGA CTG CTC TGC CTT CTT CCC ACA GGA CTG CCC GTT CGC AGC GTG      96
Leu Arg Leu Leu Cys Leu Leu Pro Thr Gly Leu Pro Val Arg Ser Val
             20                  25                  30

GAT TTT AAC CGA GGC ACG GAC AAC ATC ACC GTG AGG CAG GGG GAC ACG     144
Asp Phe Asn Arg Gly Thr Asp Asn Ile Thr Val Arg Gln Gly Asp Thr
         35                  40                  45

GCC ATC CTC AGG TGT GTG GTA GAA GAC AAG AAC TCG AAA GTG GCC TGG     192
Ala Ile Leu Arg Cys Val Val Glu Asp Lys Asn Ser Lys Val Ala Trp
     50                  55                  60

TTG AAC CGC TCT GGC ATC ATC TTC GCT GGA CAC GAC AAG TGG TCT CTG     240
Leu Asn Arg Ser Gly Ile Ile Phe Ala Gly His Asp Lys Trp Ser Leu
 65                  70                  75                  80

GAC CCT CGG GTT GAG CTG GAG AAA CGC CAT GCT CTG GAA TAC AGC CTC     288
Asp Pro Arg Val Glu Leu Glu Lys Arg His Ala Leu Glu Tyr Ser Leu
                 85                  90                  95
```

```
CGA ATC CAG AAG GTG GAT GTC TAT GAT GAA GGA TCC TAC ACA TGC TCA          336
Arg Ile Gln Lys Val Asp Val Tyr Asp Glu Gly Ser Tyr Thr Cys Ser
            100                 105                 110

GTT CAG ACA CAG CAT GAG CCC AAG ACC TCT CAA GTT TAC TTG ATT GTA          384
Val Gln Thr Gln His Glu Pro Lys Thr Ser Gln Val Tyr Leu Ile Val
        115                 120                 125

CAA GTT CCA CCA AAG ATC TCC AAC ATC TCC TCG GAT GTC ACT GTG AAT          432
Gln Val Pro Pro Lys Ile Ser Asn Ile Ser Ser Asp Val Thr Val Asn
    130                 135                 140

GAG GGC AGC AAT GTA ACC CTG GTC TGC ATG GCC AAT GGG CGC CCT GAA          480
Glu Gly Ser Asn Val Thr Leu Val Cys Met Ala Asn Gly Arg Pro Glu
145                 150                 155                 160

CCT GTT ATC ACC TGG AGA CAC CTT ACA CCA CTT GGA AGA GAA TTT GAA          528
Pro Val Ile Thr Trp Arg His Leu Thr Pro Leu Gly Arg Glu Phe Glu
                165                 170                 175

GGA GAA GAA GAA TAT CTG GAG ATC CTA GGC ATC ACC AGG GAA CAG TCA          576
Gly Glu Glu Glu Tyr Leu Glu Ile Leu Gly Ile Thr Arg Glu Gln Ser
            180                 185                 190

GGC AAA TAT GAG TGC AAG GCT GCC AAC GAG GTC TCC TCC GCG GAT GTC          624
Gly Lys Tyr Glu Cys Lys Ala Ala Asn Glu Val Ser Ser Ala Asp Val
        195                 200                 205

AAA CAA GTC AAG GTC ACT GTG AAC TAT CCA CCC ACC ATC ACA GAG TCT          672
Lys Gln Val Lys Val Thr Val Asn Tyr Pro Pro Thr Ile Thr Glu Ser
    210                 215                 220

AAG AGC AAT GAA GCC ACC ACA GGA CGA CAA GCT TCC CTC AAA TGT GAA          720
Lys Ser Asn Glu Ala Thr Thr Gly Arg Gln Ala Ser Leu Lys Cys Glu
225                 230                 235                 240

GCC TCA GCG GTG CCT GCA CCT GAC TTT GAG TGG TAC CGG GAT GAC ACC          768
Ala Ser Ala Val Pro Ala Pro Asp Phe Glu Trp Tyr Arg Asp Asp Thr
                245                 250                 255

AGG ATA AAC AGT GCA AAC GGC CTT GAG ATT AAG AGC ACT GAG GGC CAG          816
Arg Ile Asn Ser Ala Asn Gly Leu Glu Ile Lys Ser Thr Glu Gly Gln
            260                 265                 270

TCC TCC CTG ACG GTG ACC AAC GTC ACT GAG GAA CAC TAC GGC AAC TAT          864
Ser Ser Leu Thr Val Thr Asn Val Thr Glu Glu His Tyr Gly Asn Tyr
        275                 280                 285

ACC TGT GTG GCT GCC AAC AAG CTC GGC GTC ACC AAT GCC AGC CTA GTC          912
Thr Cys Val Ala Ala Asn Lys Leu Gly Val Thr Asn Ala Ser Leu Val
    290                 295                 300

CTT TTC AGA CCC GGG TCG GTG AGA GGA ATC AAC GGA TCC ATC AGT CTG          960
Leu Phe Arg Pro Gly Ser Val Arg Gly Ile Asn Gly Ser Ile Ser Leu
305                 310                 315                 320

GCC GTA CCA CTG TGG CTG CTG GCA GCG TCC CTG TTC TGC CTT CTC AGC         1008
Ala Val Pro Leu Trp Leu Leu Ala Ala Ser Leu Phe Cys Leu Leu Ser
                325                 330                 335

AAA TGT                                                                 1014
Lys Cys
```

(2) INFORMATION FOR SEQ ID NO:8:

(i) SEQUENCE CHARACTERISTICS:
        (A) LENGTH: 338 amino acids
        (B) TYPE: amino acid
        (C) STRANDEDNESS: single
        (D) TOPOLOGY: linear (xi) SEQUENCE DESCRIPTION: SEQ ID NO:8:

```
Met Val Gly Arg Val Gln Pro Asp Arg Lys Gln Leu Pro Val Leu
1               5                   10                  15

Leu Arg Leu Leu Cys Leu Leu Pro Thr Gly Leu Pro Val Arg Ser Val
```

```
                20                  25                  30
Asp Phe Asn Arg Gly Thr Asp Asn Ile Thr Val Arg Gln Gly Asp Thr
            35                  40                  45
Ala Ile Leu Arg Cys Val Leu Glu Asp Lys Asn Ser Lys Val Ala Trp
 50                  55                  60
Leu Asn Arg Ser Gly Ile Ile Phe Ala Gly His Asp Lys Trp Ser Leu
65                  70                  75                  80
Asp Pro Arg Val Glu Leu Glu Lys Arg His Ser Leu Glu Tyr Ser Leu
                85                  90                  95
Arg Ile Gln Lys Val Asp Val Tyr Asp Glu Gly Ser Tyr Thr Cys Ser
                100                 105                 110
Val Gln Thr Gln His Glu Pro Lys Thr Ser Gln Val Tyr Leu Ile Val
            115                 120                 125
Gln Val Pro Pro Lys Ile Ser Asn Ile Ser Ser Asp Val Thr Val Asn
        130                 135                 140
Glu Gly Ser Asn Val Thr Leu Val Cys Met Ala Asn Gly Arg Pro Glu
145                 150                 155                 160
Pro Val Ile Thr Trp Arg His Leu Thr Pro Thr Gly Arg Glu Phe Glu
                165                 170                 175
Gly Glu Glu Glu Tyr Leu Glu Ile Leu Gly Ile Thr Arg Glu Gln Ser
                180                 185                 190
Gly Lys Tyr Glu Cys Lys Ala Ala Asn Glu Val Ser Ser Ala Asp Val
            195                 200                 205
Lys Gln Val Lys Val Thr Val Asn Tyr Pro Pro Thr Ile Thr Glu Ser
        210                 215                 220
Lys Ser Asn Glu Ala Thr Thr Gly Arg Gln Ala Ser Leu Lys Cys Glu
225                 230                 235                 240
Ala Ser Ala Val Pro Ala Pro Asp Phe Glu Trp Tyr Arg Asp Asp Thr
                245                 250                 255
Arg Ile Asn Ser Ala Asn Gly Leu Glu Ile Lys Ser Thr Glu Gly Gln
                260                 265                 270
Ser Ser Leu Thr Val Thr Met Val Thr Glu Glu His Tyr Gly Asn Tyr
            275                 280                 285
Thr Cys Val Ala Ala Asn Lys Leu Gly Val Thr Asn Ala Ser Leu Val
        290                 295                 300
Leu Phe Arg Pro Gly Ser Val Arg Gly Ile Asn Gly Ser Ile Ser Leu
305                 310                 315                 320
Ala Val Pro Leu Trp Leu Leu Ala Ala Ser Leu Leu Cys Leu Leu Ser
                325                 330                 335
Lys Cys (2) INFORMATION FOR SEQ ID NO:9:

(i) SEQUENCE CHARACTERISTICS:
        (A) LENGTH: 21 amino acids
        (B) TYPE: amino acid
        (C) STRANDEDNESS: single
        (D) TOPOLOGY: linear (xi) SEQUENCE DESCRIPTION: SEQ ID NO:9:

Val Arg Ser Val Asp Phe Asn Arg Gly Thr Asp Asn Ile Thr Val Arg
 1               5                  10                  15

Gln Gly Asp Thr Ala
                20
```

```
(2) INFORMATION FOR SEQ ID NO:10:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:10:

Asp Phe Asn Arg Gly Thr Asp
 1               5

(2) INFORMATION FOR SEQ ID NO:11:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:11:

Ile Thr Val Arg Gln Gly Asp
 1               5

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:12:

GAYTTYAAYC GNGGNACNGA Y                                              21

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:13:

GAYTTYAAYA GRGGNACNGA Y                                              21

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:14:

ATHACNGTNC GNCARGGNGA Y                                              21

(2) INFORMATION FOR SEQ ID NO:15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:15:

ATHACNGTNA CGRCARGGNG AY                                             22
```

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:16:

GAYTTYAAYC GNGGNACNGA Y                                           21

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:17:

TGCCAGCAGC CACAGTGGTA                                            20

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:18:

CGAATCCAGA AGGTGGATGT                                            20

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:19:

TGCCAGCAGC CACAGTGGTA                                            20

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:20:

CGAATCCAGA AGGTGGATGT                                            20

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:21:

GTAGTGTTCC TCAGTGACGT                                            20

(2) INFORMATION FOR SEQ ID NO:22:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:22:

CGGAATTCAT GGTCGGGAGA GTTCAACC                                        28

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:23:

GTAGTGTTCC TCAGTGACGT                                                  20

(2) INFORMATION FOR SEQ ID NO:24:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:24:

CGGAATTCAT GGTCGGGAGA GTTCAACC                                        28

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:25:

TCAACCAGGC CACTTTCGAG                                                  20

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:26:

TCTAAGAGCA ATGAAGCCAC                                                  20

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:27:

TTAACATTTG CTGAGAAGGC                                                  20

(2) INFORMATION FOR SEQ ID NO:28:

```
    (i) SEQUENCE CHARACTERISTICS:
         (A) LENGTH: 39 base pairs
         (B) TYPE: nucleic acid
         (C) STRANDEDNESS: single
         (D) TOPOLOGY: linear (xi) SEQUENCE DESCRIPTION: SEQ ID NO:28:

CCGAAGCTTC TGCAGTATGC CTTCCTATCC ATGTGTATG                           39

(2) INFORMATION FOR SEQ ID NO:29:

(i) SEQUENCE CHARACTERISTICS:
         (A) LENGTH: 49 base pairs
         (B) TYPE: nucleic acid
         (C) STRANDEDNESS: double
         (D) TOPOLOGY: linear (xi) SEQUENCE DESCRIPTION: SEQ ID NO:29:

ATATCTAGAT AGTGGTACCG AGTTGTTCCG CGGTGGACTG CGTGTGCGC                49
```